(12) United States Patent
Sasaki

(10) Patent No.: US 6,753,295 B1
(45) Date of Patent: Jun. 22, 2004

(54) PLANT ACTIVATOR, PROCESS FOR PRODUCING THE SAME, ACTIVATION METHOD, ACTIVITY PROMOTER AND METHOD FOR APPLYING THE PROMOTER

(75) Inventor: Yasuharu Sasaki, Room 202, Crest Tage Fushimi, 1-17, Minami 18 jonisi 15-chome, Chuo-ku, Sapporo-shi Hokkai-do 064-0918 (JP)

(73) Assignees: Yasuharu Sasaki, Hokkai-do (JP); Hokkaido Green Kosan, Incorporated, Hokkai-do (JP)

( * ) Notice: Subject to any disclaimer, the term of this patent is extended or adjusted under 35 U.S.C. 154(b) by 0 days.

(21) Appl. No.: 09/958,212
(22) PCT Filed: Apr. 6, 2000
(86) PCT No.: PCT/JP00/02239
§ 371 (c)(1), (2), (4) Date: Dec. 20, 2001
(87) PCT Pub. No.: WO00/61591
PCT Pub. Date: Oct. 19, 2000

(30) Foreign Application Priority Data

Apr. 8, 1999  (JP) ........................................... 11/101398
Oct. 5, 1999  (JP) ........................................... 11/284734
Jan. 25, 2000  (JP) ......................................... 2000/15680

(51) Int. Cl.⁷ ...................... A01N 63/02; A01N 37/06; A01N 37/30
(52) U.S. Cl. .................... 504/117; 435/254.6; 504/142; 504/149
(58) Field of Search ................................. 504/117, 142, 504/149; 435/254.6

(56) References Cited

U.S. PATENT DOCUMENTS

| | | | | |
|---|---|---|---|---|
| 4,828,600 A | * | 5/1989 | McCabe et al. | 71/76 |
| 5,084,272 A | * | 1/1992 | Speakman et al. | 424/93 |
| 5,330,912 A | * | 7/1994 | Toet et al. | 435/254.1 |
| 5,422,107 A | | 6/1995 | Kubota | 424/93.5 |
| 5,474,926 A | * | 12/1995 | Harman et al. | 435/200 |

FOREIGN PATENT DOCUMENTS

| | | |
|---|---|---|
| EP | 0 124 388 | 11/1984 |
| EP | 0 387 640 | 9/1990 |
| JP | 7-101815 | 4/1995 |

OTHER PUBLICATIONS

Database WPI, Section Ch, Week 198922, Derwent Publications Ltd., London, GB; AN 1989–160785 XP002201211 & Abstract of JP 01 102010.

* cited by examiner

Primary Examiner—S. Mark Clardy
(74) Attorney, Agent, or Firm—Wenderoth, Lind & Ponack, LLP

(57) ABSTRACT

A plant is activated and the activity is promoted by using a product of *Trichoderma harzianum* SK-5-5 strain. The activation of a plant and the promotion of the activity can be achieved by culturing *Trichoderma harzianum* SK-5-5 strain in a solid medium and extracting its product, or by applying the conidiospores of the above strain.

2 Claims, 33 Drawing Sheets

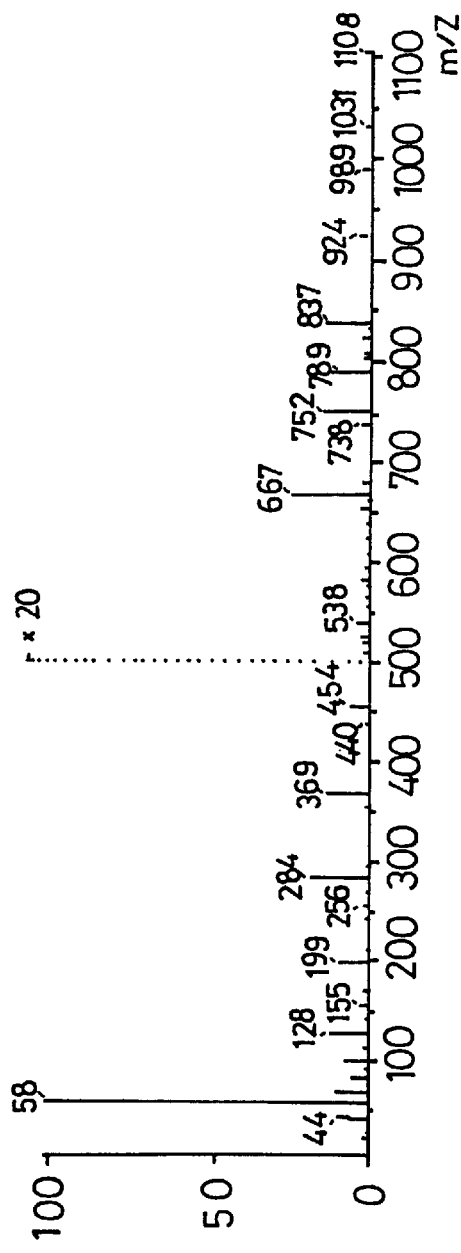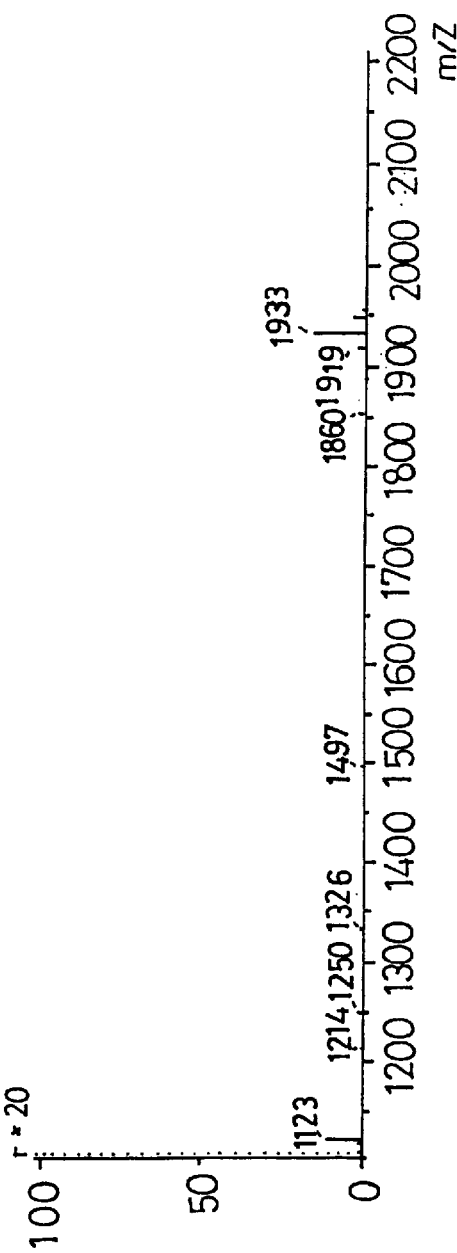
FIG. 5 (a)
FIG. 5 (b)

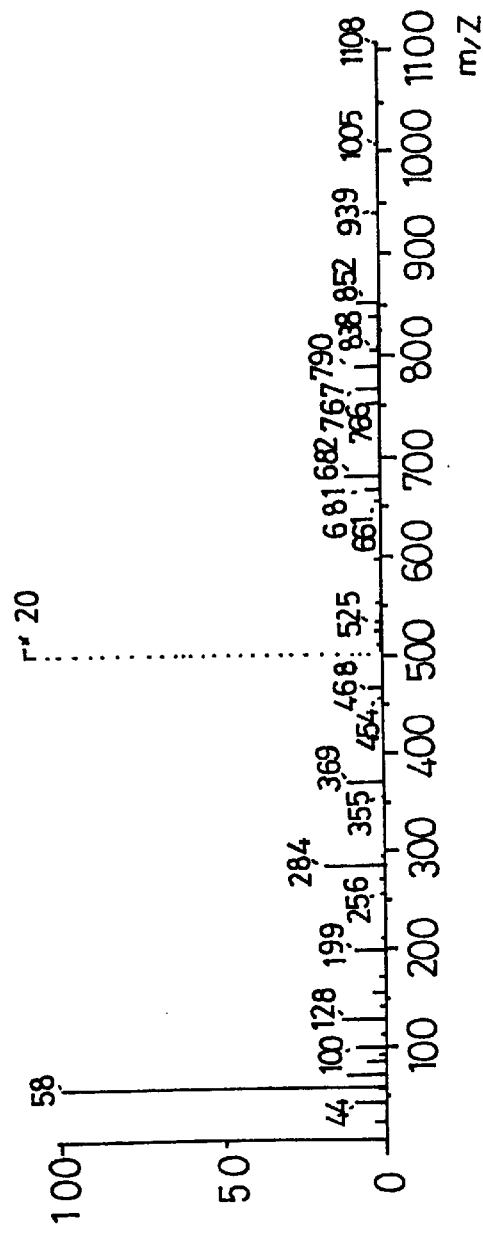
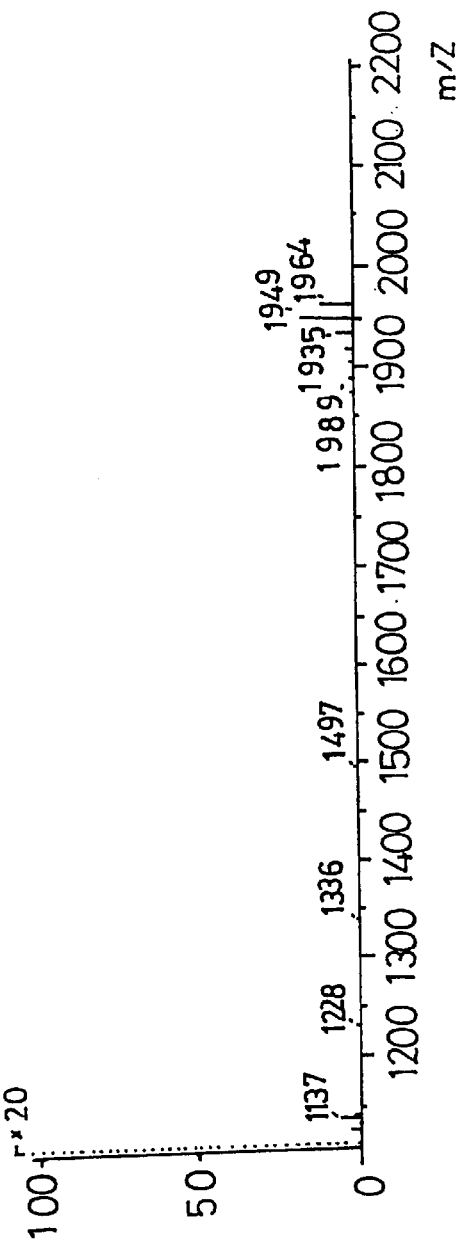

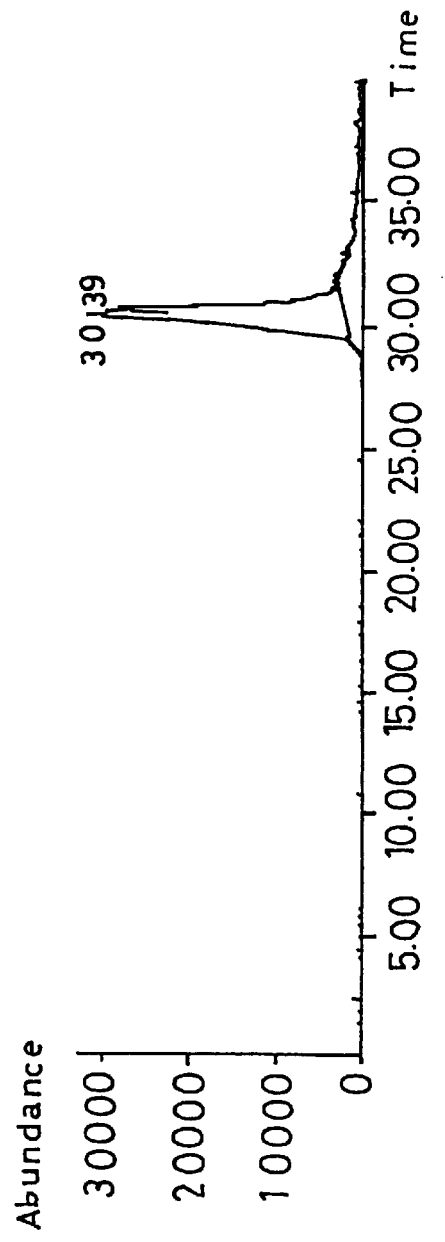
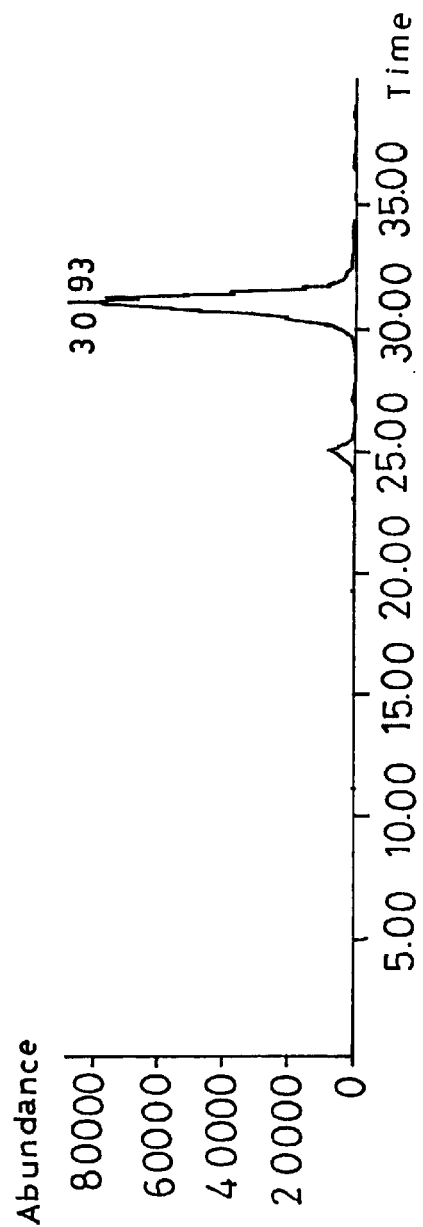
FIG. 29 (a)
FIG. 29 (b)

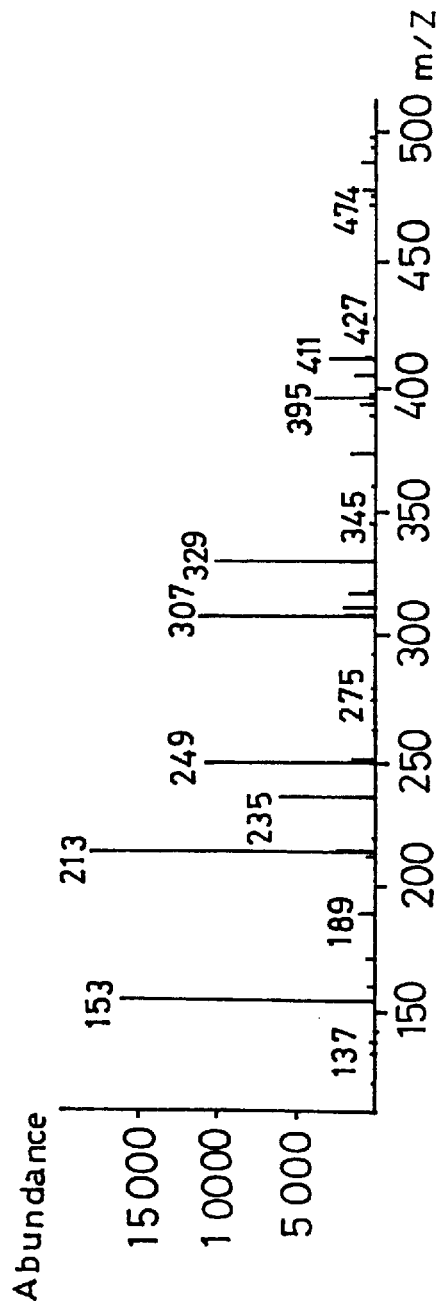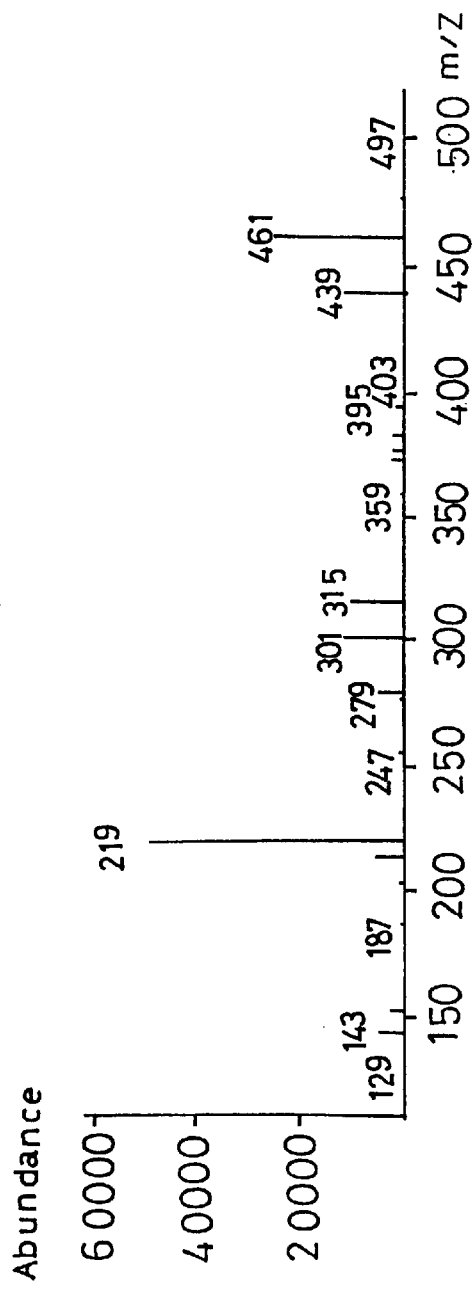
FIG. 30 (a)
FIG. 30 (b)

|   | R1 | R2 |
|---|---|---|
| 1 | COOH | H |
| 2 | COOCH3 | H |
| 3 | COOCH3 | COCH3 |

Correlation between bulb diameter and leave area

PLANT ACTIVATOR, PROCESS FOR PRODUCING THE SAME, ACTIVATION METHOD, ACTIVITY PROMOTER AND METHOD FOR APPLYING THE PROMOTER

TECHNICAL FIELD

This invention relates to a plant activator extracted from a culture of *Trichoderma harzianum* SK-5-5 strain for the purpose of obtaining a substance having antimicrobial properties against filamentous fungi and microorganisms, as well as a process for producing the same.

Further, this invention relates to a method of activating a plant, a plant activation promoter and a method of applying said promoter for the purpose of conferring resistance to disease-causing bacteria on plant roots, stems, leaves etc. by a substance produced by the conidiospores of *Trichoderma harzianum* SK-5-5 strain.

BACKGROUND ART

The Trichoderma genus are filamentous fungi used practically as microbial agricultural chemical for controlling crop damage, and *Trichoderma lignourum* has been registered as an agricultural chemical for controlling tobacco white-silk disease (Agricultural chemical Registration No. 7023). Further, a microbial agricultural chemical (F-stop) comprising *Trichoderma harzianum* as an active ingredient effective against damping-off and seedling withering of vegetables has been registered in England and France.

The necessity for controlling crop damage by agricultural chemical in a smaller amount for maintaining the ecosystem has strongly been advocated in recent years, and in particular a method of biological control is considered to have less adverse effect on the environment, and thus extensively studied.

Some bacteria separated from plant roots and rhizosphere and fungi promote plant growth, and are called "plant growth-promoting rhizobacteria (PGPR)" and "plant growth-promoting fungi (PGPF)", respectively.

It is known that the useful microorganism in the rhizosphere, PGPR and PGPF, not only promote plant growth but also control various kinds of crop damages in soil. Recently, it was also revealed that they control not only crop damage in soil but also crop damage over the ground, and it was introduced that the PGPR and PGPF were found to be involved in inducing general plant resistance ("Kongetsu no Nogyo" (Agriculture of This Month), June issue, 1999).

It is reported that bacteria such as Phoma, Trichoderma, Fusarium, Penicillium and Sterile, which were separated and screened from the Korean lawn grass, bring inductive resistance against anthracnose in cucumber ("Kongetsu no Nogyo" (Agriculture of This Month), June issue, 1999).

This invention was made to solve the problem of obtaining a substance having antimicrobial properties against plant disease-causing bacteria, and *Trichoderma harzianum* SK-5-5 microorganism was separated from soil in the Tokachi District in Hokkaido, Japan. This microorganism has a wide antagonistic spectrum against soil infectious disease-causing filamentous fungi estimated to account for 80% of the plant disease-causing bacteria. This microorganism is now under development as a microbial agricultural chemical (pharmaceutical preparation of the living microorganism) against microorganisms of the genus *Rhizoctonia* causing brown batch and large batch in lawn. The antagonistic action of above-described *Trichoderma harzianum* SK-5-5 strain is to accelerate cytoplasmic aggregation upon contacting with hyphae and coiling thereof, thus killing the disease-causing bacteria. As a result of observation of the outward appearance with time, it is estimated that its activity is brought about upon contacting with hyphae, and is not so high as that of an antibiotic produced by e.g. Penicillium sp. giving rise to a circle of inhibited growth on medium.

Above action of cytoplasmic aggregation is consider to bring about a certain kind of substance produced by *Trichoderma harzianum* SK-5-5 strain, and the first object of the present invention is to reveal this substance.

*Trichoderma harzianum* SK-5-5 strain used in this invention has been deposited under deposition number "Bikoken Microbial Deposition No. 13327" with the National Institute of Bioscience and Human-Technology, Agency of Industrial Science and Technology, Japan (address: Azuma 1-1-3, Tsukuba-shi, Ibaraki Pref., JAPAN) (deposited date:Dec. 9, 1992, depositary: Hokkaido Green Kosan, Incorporated). The transfer of original deposition to international deposition under the Budapest treaty was requested on Dec. 9, 1992, and said microorganism is given deposition number BP-4346.

The above-described conventional PGPR and PGPF show efficacy for specific plants (e.g. cucumber) against anthracnose. There is some possibility of revealing their effectiveness for other plants against other disease-causing bacteria by improvements of application method e.g. in future, but it is still a problem in future to reveal their effectiveness for specific plants against specific disease-causing bacteria.

However, the thinking form of conventional biological agricultural chemical, that is merely killing disease-causing bacteria tends to chenge the way of providing conferring resistance on the whole of roots and stems of plant. This matter includes an important suggestion about plant cultivation in future.

The present inventors found that *Trichoderma harzianum* SK-5-5 strain is promising the future of biological agricultural chemical through various experiments, and the present invention was completed as a result of further examination of the method, target plants and so on. The present invention is very promising one exerting a great influence on plant cultivation in future, and will undoubtedly serve as an important means to support agriculture in future, etc.

DISCLOSURE OF INVENTION

The present inventors estimated that the action of cellular aggregation (antimicrobial properties) is brought about a substance produced by *Trichoderma harzianum* SK-5-5 strain, and as a result of cultivation, purification and identification of said microorganism, they could successfully obtain a substance having antimicrobial properties against filamentous fungi or microorganisms.

It was revealed that the formed substance which was obtained by multipying the conidiospores of *Trichoderma harzianum* SK-5-5 strain in the soil for plant cultivation, was activated the roots and stems of various plants and was improved the resistance of the plants. Thereby the problem of the prior art is progressively solved and the practicality is established.

That is, the invention is directed to activator is a plant activator having antimicrobial properties against filamentous fungi, which is a substance extracted from *Trichoderma harzianum* SK-5-5 strain cultured on a solid medium. Another invention is a plant activator having antimicrobial properties against a kind of microorganism (*Staphylococcus aureus* 209p), which is a substance extracted from *Trichoderma harzianum* SK-5-5 strain cultured in a liquid medium.

The invention directed to the production process is a process for producing a plant activator, which comprises inoculating *Trichoderma harzianum* SK-5-5 strain onto a solid medium, subjecting it to stationary cultivation at 25 to 30° C. for 7 to 15 days and then extracting to give said activator, and as well as a process for producing a plant activator, which comprises inoculating *Trichoderma harzianum* SK-5-5 strain into a liquid medium, subjecting it to shake cultivation at 25 to 30° C. for 4 to 10 days and then extracting to give said activator.

As the solid medium used in this invention, a rice medium was used. The rice medium is a solid medium composed of 100% rice, 3% soybean cake and 10% sterilized water, and the sterilized water was added to prevent the surface of the medium from being dried during cultivation.

The liquid medium used in this invention was composed of 3.0 to 5.0% glucose, 0.5% polypeptone, 0.8% NaCl, 0.2% yeast extract and 1.0% calcium carbonate.

It was revealed that depending on whether the solid medium or liquid medium is used, a different substance is formed due to the characteristics. The mechanism thereof is not revealed, but a different substance is formed due to the difference action in stimuli and other against *Trichoderma harzianum* SK-5-5 strain and the characteristics on materials constituting the medium. It is considered highly possible that a similar substance can also be formed in the medium other than rice medium or liquid medium, and there are still a large number of problems to be studied for improvements in efficiency of formation, etc.

The invention directed to the method of activation relates to a method of activating a plant, which comprises applying conidiospores of *Trichoderma harzianum* SK-5-5 strain in plant cultivation and allowing them to be present in soil for activating the plant, as well as a method of activating a plant, which comprises applying conidiospores of *Trichoderma harzianum* SK-5-5 strain in plant cultivation, multiplying them in soil for activating the plant, and sustaining production of a substance having antimicrobial properties against filamentous fungi. Further, the present invention relates to a method of activating a plant, which comprises applying conidiospores of *Trichoderma harzianum* SK-5-5 strain in plant cultivation and allowing them to be present in soil for activating the plant under the conditions where conidiospore growth is promoted. The application of conidiospores involves treatment of plant seeds therewith, incorporation of conidiospores into soil, spraying conidiospores, sprinkling water or laying. Under the conditions where conidiospore growth is promoted, the soil temperature is kept at 15 to 30° C. and the water content is kept at 30% or more, and other conditions for growth promotion involve air permeation or air entrainment, enabling growth in soil.

Another invention is directed to a plant activator comprising conidiospores of *Trichoderma harzianum* SK-5-5 strain adhering to porous ceramic particles or other carriers and to a plant activator comprising *Trichoderma harzianum* SK-5-5 strain or conidiospores thereof mixed in, or adhering to, aseptic inorganic particles to be mixed with other particles. Further, the present invention relates to a plant activator prepared by culturing conidiospores of *Trichoderma harzianum* SK-5-5 strain, separating a suitable amount of them together with the medium, permitting thereof and nutrients (e.g. chitosan) to adhere to germ-free porous particles, and then packaging a predetermined amount of thereof. And the present invention relates and to a plant activator prepared by multiplying conidiospores of *Trichoderma harzianum* SK-5-5 strain in a liquid medium, permitting them and nutrients to adhere to germ-free porous particles, and then packaging a predetermined amount of thereof.

A further other invention relates to a method of applying said plant activator, which comprises mixing the plant activator with soil for seedlings or spraying it onto soil or a field at a seedling stage. In this case, the activator is applied such that $5 \times 10^4$/g to $5 \times 10^9$/g of *Trichoderma harzianum* SK-5-5 microorganisms are sprayed at a density of 5 to 100 g/m$^2$ field or mixed at a density of 5 to 100 g/m$^3$ compost.

The above-described plant in the present invention includes sugar beet, melon, corn, paddy rice, cabbage and onion. But it is confirmed that the present invention is effective for any plants whose roots, stems, leaves and fruits are to be harvested, and effects such as higher yield, higher sugar level and other usefulness are revealed.

By cultivating conidiospores of *Trichoderma harzianum* SK-5-5 strain in the present invention and by examining their isolated and purified products by UV absorption, mass spectrometry and NMR, it was judged that the products are polypeptides of peptibols type containing Aib (α-aminoisobutyric acid). A peptibols-type antibiotic contains α-aminoisobutyric acid (Aib) in the amino acid sequence thereof, which is characterized in that the N-terminus is an acetyl group and the C-terminus is an amino alcohol linkage (terminating often at a phenylalaniol group). It was estimated by mass spectrometry that components A, B and D of the purified products of this invention have following partial amino acid sequences, and there is no agreement between these partial structures and the amino acid sequences of existing peptibols. Thus, the present products are suggested novel peptibols. Component E could not be judged because of estimation difficulty of its amino acid sequence. UV absorption wavelength: The 4 components of terminal absorption are shown.

Component A=1933
Component B=1949 or 1964
Component D=1810
Component E=1829

Estimated Structures:

Component A: Ac-Aib-Ala-Aib-Aib-Aib-Aib-Gln-Aib-Aib- . . .

Component B: Ac-Aib-Ala-Aib-Aib-Val-Aib-Gln-Aib-Aib- . . .

Component D: Ac-Aib-Ala-Aib-Aib-Aib- . . .

As described above, it is recognized that the formed products have novel amino acid sequences, which are absorbed through plant roots into stems and leaves, to disappear finally. Accordingly, it is not evident that the formed products are present in roots, stems and leaves of the plant at a harvest stage. But it is estimated that the formed products cause a certain change to DNA of plant or remain in the plant at an early stage (young stems after germination) of absorption into the plant. This is because the plant which has attained antimicrobial properties once, retains the antimicrobial properties even after differentiation and formation of roots, stems etc. Accordingly, this phenomenon is similar to that of immunization (activation), so that if the present products are applied to seedlings or relatively young plants (undergoing substantial growth), necessity for additional application is eliminated. The reason is that the antimicrobial properties are activated to retain throughout their life when the activity is formed.

By mixing conidiospores of *Trichoderma harzianum* SK-5-5 strain of this invention in soil at a seedling stage or during seeding, the formed substances formed are increased together with the growth of conidiospores. It is confirmed to maintain antimicrobial properties even if the stage where the roots or fruits of the grown plant are harvested (e.g., 1 to 6 months after seeding), because the formed substances absorb through roots to reach stems and leaves and confer antimicrobial properties on the whole of plant (like immunization). Accordingly, many plants could be endowed with antimicrobial properties by only one treatment (spraying or other means), to achieve the object sufficiently.

In the present invention, the carriers of conidiospores are porous ceramic particles (e.g. particles of healstone) subjected to immersion in a chitosan solution followed by evaporating water therein. The size of these particles is not particularly limited, but the diameter of these particles prefers about 0.5 to 5 mm for easy handling. Above-described carriers are not limited to porous ceramic particles (natural or artificial), and may be used any materials not to exert a bad influence of conidiospores.

Previously cultured $5 \times 10^4$/g to $5 \times 10^9$/g of *Trichoderma harzianum* SK-5-5 microorganisms are allowed to adhere at a density of 5 to 100 g/m$^2$ to ceramic particles. In this case, the particles may be sprayed with conidiospores together with water, but sprinkling of water is conducted for the purpose of providing water or permitting conidiospores to be permeated uniformly and dispersed uniformly in soil.

When the amount of *Trichoderma harzianum* SK-5-5 microorganisms is less than $5 \times 10^4$/g, the microorganisms grow unless their propagation is inhibited, but because there is the case where the microorganisms do not grow for some reasons, the amount of the microorganisms may be changed if necessary. However, it is considered to grow the microorganisms in harmony with plant growth and obtain the necessary amount of the formed substances even if the smaller amount (e.g. less than 5 g) under the control of the environment, because microbial propagation is significantly varied on the environment.

The upper limit of the microbial amount is defined to be not higher than $5 \times 10^9$/g microorganisms because it is not necessary from the relationship with formed substances. When the conditions for microbial growth are bad, it is necessary to apply the microorganisms at relatively high density but not to extend $5 \times 10^9$/g.

In this invention, *Trichoderma harzianum* SK-5-5 strain is applied usually in the form of conidiospores, but it is prefer to apply in the form of spores with thick membrane in the case of the environment at the time of application is severe (e.g. high or low temperature).

In the invention described above, when *Trichoderma harzianum* SK-5-5 strain is cultured in solid medium or liquid medium or other medium, and its products are extracted and applied as plant activator, e.g. 0.1 to 1 g/m$^2$ is necessary.

Further when the conidiospores are to be sprayed, the density of the conidiospores should be higher than the lower-limit density (e.g. $5 \times 10^4$/g) at which the conidiospores can grow.

The plant activator of this invention may be applied only once, and thereafter not be applied until harvest. This point is different from general agricultural chemical. The mechanism is not clear, but it is estimated that the plant activator exerts a certain influence on DNA of plant or the formed substances remain in a very small amount in plant roots, stems and leaves, and bring about the characteristics described above.

It was confirmed that conidiospores grow sufficiently and saturate and thereafter the activity of the conidiospores is rapidly lost and finally extinguished, in e.g. a field when conidiospores are applied in the invention described above. As a matter of course, some conidiospores may still remain and grow again under good growth conditions.

In the present invention, *Trichoderma harzianum* SK-5-5 is cultured in solid medium or liquid medium, and components A, B, C, D and E are isolated and purified from the product, and these active substances are novel substances each having a novel amino acid sequence, and their molecular weights are as follows: component A=192, component B=206, component C=168, $D_1$=154, and $D_2$=220, and their amino acids, or amino acids therearound, are estimated to be effective for plant activation.

It is confirmed that the intended object can be achieved by applying conidiospores of *Trichoderma harzianum* SK-5-5 strain (by mixing in soil or applying to the rhizosphere) at a predetermined density (e.g. $5 \times 10^5$/g or more). There must be the optimum component or mixing ratio depending on plant.

Accordingly, *Trichoderma harzianum* SK-5-5 strain is cultured in a large scale by conventional method, and the formed substances are isolated and purified, whereby the plant activator can be obtained. As the formed substances, the components A, B, C, D and E have been identified.

The invention described above is effective for various kinds of plants, but as a result of experiments (including under experiments), it was confirmed to effect for paddy rice, corn, sugar beet, melon, potato, sweet potato, strawberry, onion and cabbage.

In this invention, it is recognized to have resistance to filamentous fungi as shown in Table 2, when *Trichoderma harzianum* SK-5-5 strain is cultured in a solid medium.

Further, it is recognized to effect against bacteria as shown in Table 2 when *Trichoderma harzianum* SK-5-5 strain is cultured in a liquid medium.

According to this invention, plant is activated to improve its roots, stems and leaves, to prevent diseases and confer resistance to disease-causing bacteria, when *Trichoderma harzianum* SK-5-5 strain is mixed in a suitable amount in bed soil at early growth stage of plant, or applied to rhizosphere by sprinkling and so on during plant growth. Accordingly, there arise various effects including not only significant reduction in diseases during growth, but also promotion of plant growth, increase in yield, and improvement in sugar level.

It is estimated that above-mentioned effects are attributable to the formed substances (e.g. novel amino acids) in conidiospores of *Trichoderma harzianum* SK-5-5 strain. Because it is recognized that the conidiospores disappear after growth and the formed substances disappear at the final stage of plant growth, no influence has in any meanings and no bad influence is not found even if they are continuously used. Further, the formed substances described above are recognized to comprise novel amino acids or surrounding substances, and are thus nontoxic even if they remain in a very small amount in plant leaves and stems.

*Trichoderma harzianum* SK-5-5 strain of this invention is propagated in soil so that when the environmental conditions are suitable for propagation, even if the concentration of the initial spray is not sufficient, the microorganisms will supply a necessary amount of formed substances through propagation, and disappear naturally after achieving the intended object. Thus, there are no possibility of influence not only on the human body but also soil, plants, environmental disruption etc. It is estimated that crops hardly subjected to repeat cultivation can solve the problem of disadvantage of repeat cultivation.

BRIEF DESCRIPTION OF DRAWINGS

FIG. 5(*a*) and (*b*) show mass spectroscopy of component A;

FIG. 8(*a*) and (*b*) show mass spectrometry of component B;

FIG. 29($a$) is a profile of component D1 detected at UV λ230 nm

FIG. 29($b$) is a profile of component D2 having terminal UV absorption and detected at a RT different by 0.6 from that of component D1;

FIG. 30($a$) shows mass spectrometry of component D1 detected in FIG. 29;

FIG. 30($b$) shows mass spectrometry of component D2 detected in FIG. 29;

BEST MODE FOR CARRYING OUT THE INVENTION

EXAMPLE 1

(Test Microorganism)

*Trichoderma harzianum* SK-5-5

Figure 1:
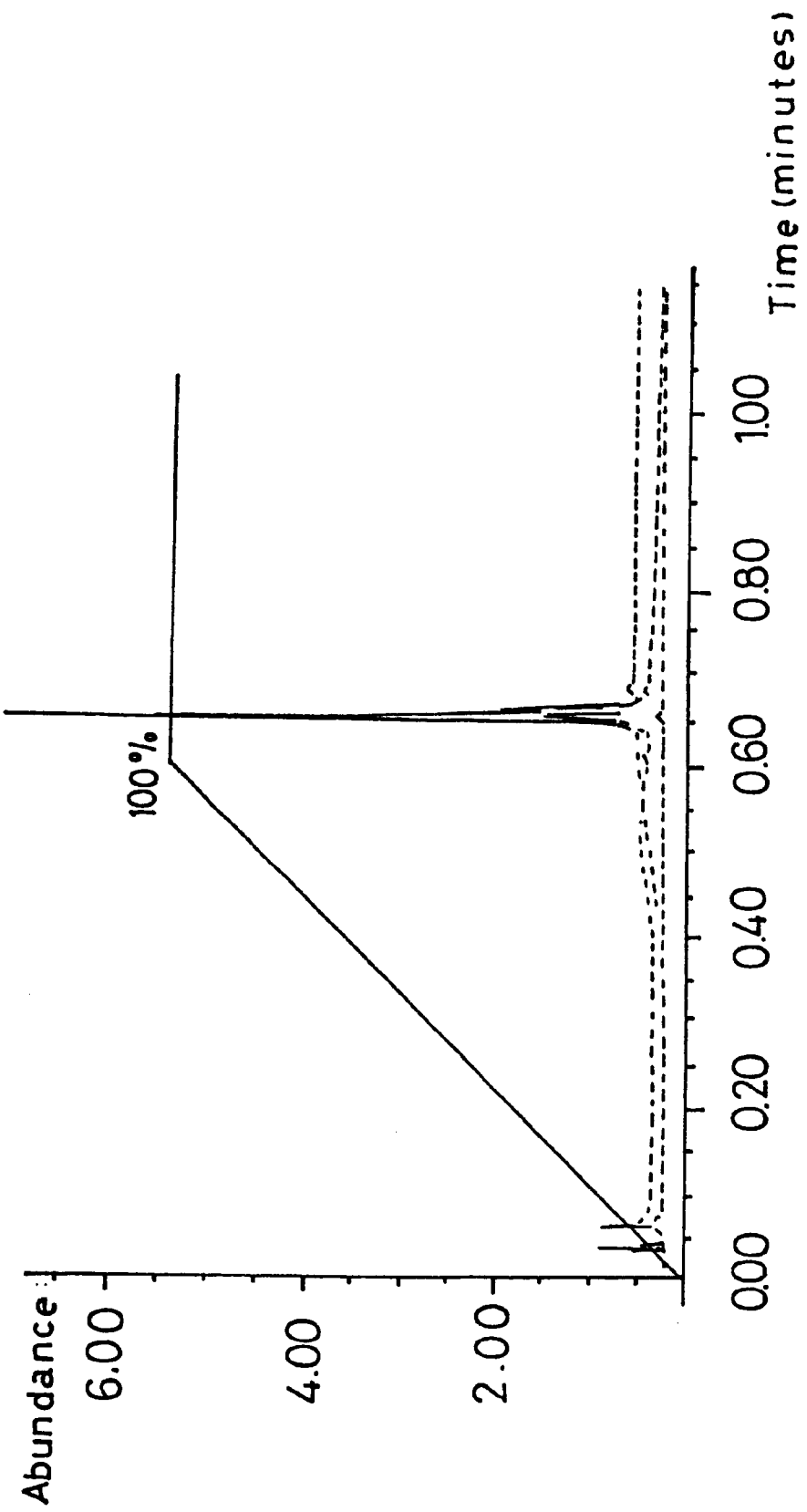
FIG. 1 is a HPLC profile of a cultivation of microorganism of this invention in medium A.

As the test microorganism, one slant culture of the microorganism in agar medium was received in January 1997 from Hokkaido Green Kosan, Incorporated. The test microorganism was inoculated onto the following slant medium, cultured at 28° C. for 5 days and then kept in cold storage.

| Composition of the agar slant medium | |
|---|---|
| Auto meal | 5.0% |
| Sucrose | 5.0% |
| Agar | 1.0% |
| Kept in cold storage after cultivation at 28° C. for 5 days | |

(Cultivation)

Cultivation was conducted using two kinds of mediums, that is, a rice medium (medium A) and a liquid medium (medium BI), in a 500-ml Erlenmeyer flask. Stationary cultivation at 28° C. was conducted for medium A (during cultivation, 10 ml sterilized water was added), and shake cultivation at 28° C. at 270 rpm was conducted for medium BI.

| Medium composition: Medium A | |
|---|---|
| Rice | 100% |
| Soybean cake | 3% |
| Sterilized water | 10% |
| Medium composition: Medium BI | |
| Glucose | 5.0% |
| Polypeptone | 0.5% |
| NaCl | 0.8% |
| Yeast extract | 0.2% |
| Calcium carbonate | 1.0% |

(Assay Method)

The following microorganisms were assayed in vitro by the paper disk plate method.

(1) *Rhizoctonia solani* (AG-1IA)

As the assay medium, a medium composed of 1.3% PDA (Nissui) and 0.002% chloramphenicol was used. The tips of hyphae of Rhizoctonia were bored by a cork borer and placed in the middle of the plate medium. A paper disk impregnated with broth was placed thereon, and the elongation of the hyphae was observed.

(2) *Botrytis cinerea*

As a assay medium, the medium composed of 20.0% potato-extract, 2.0% sucrose and 1.5% agar was used. For assay, the sample was placed on a paper disk, air-dried and placed on a Petri dish. The Petri dish was placed in an incubator and incubated, and whether or not a circle of inhibited growth was formed around the paper disk was observed.

(3) Microorganisms Assayed for Antimicrobial Spectrum

| The antimicrobial spectrum was measured using the following microorganisms: |
|---|
| *Bacillus subtilis* ATCC6633 |
| *Micrococcus luters* ATCC6633 |
| *Staphylococcus aureus* 209P |
| *Escherichia coli* NIHJ |
| *Saccharomyces cerevisiae* SHY3 |
| *Candida albicans* M9001 |
| *Candida pseudotropicalis* M9035 |
| *Cryptococcus neoformans* M9010 |
| *Debaryomyces hansenii* M9011 |
| *Trigonopsis variabilis* M9031 |
| *Shizosaccharomyces pombe* M9025 |
| *Hansenula schneggi* IAM4269 |

(Cultivation Method)

(1) Cultivation Method Using Medium A

Active Substances From *Rhizoctonia Solani* (AG-1IA)

Isolation and Purification of Active Substances of Cultivated Extraction from Medium A Against Filamentous Fungus *Rhizoctonia solani* (AG-1IA)

100 g rice and 3 g soybean cake were added to a 500-ml Erlenmeyer flask containing medium A (1 kg rice medium), and the medium was prepared in 10 flasks under the same conditions. After sterilization, the microorganism was inoculated into the medium via Eaze (phonetic trans.), subjected to stationary cultivation at 28° C. for 10 days (Each flask was shaken several times so that the microorganism grew well. When the surface of the medium came to be dried, sterilized water was added), and then subjected to extract with adding 2 liter of 50% aqueous acetone. 2 liter liquid extracted with 50% acetone was thus obtained.

(2) Cultivation Method Using Medium B
Active Substances Against *Staphylococcus Aureus* 209P

TABLE 1

Examination of Mediums

| Ingredients | Division | | | |
|---|---|---|---|---|
| | I | II | III | IV |
| Glucose | 5.0% | 5.0% | 5.0% | 3.0% |
| Polypeptone | 0.5% | 1.0% | 2.0% | 3.0% |
| NaCl | 0.8% | 0.8% | 0.8% | 0.8% |
| Yeast extract | 0.2% | 0.2% | 0.2% | 0.2% |
| Calcium carbonate | 1.0% | 1.0% | 1.0% | 1.0% |
| C/N | C = 2.0 | C = 2.0 | C = 2.0 | C = 2.0 |
| | N = 0.089 | N = 0.0164 | N = 0.314 | N = 0.464 |
| | 22 | 11 | 6.4 | 2.5 |

For the purpose of producing a larger amount of an antimicrobial active component in medium B as the liquid medium, four kinds of mediums I to IV having a different ratio of a nitrogen source to a carbon source in the medium composition were comparatively examined. The microorganism was cultivated for 5 days in two 500-ml Erlenmeyer flasks for each medium, and each resultant was concentrated 5-fold and used in assay.

(3) Cultivation Method Using Medium BI

As a result of examination of the mediums, the cultivation was conducted by using medium BI.

100 ml medium BI (5.0% glucose, 0.5% polypeptone, 0.8% NaCl, 0.2% yeast extract, 1.0% calcium carbonate) was prepared in a 500-ml Erlenmeyer flask. After the medium was sterilized, the microorganism was inoculated into it. And then shake cultivation was conducted at 28° C. for 5 days. The culture liquid, 1.5 liter in total, was mixed with an equal volume of acetone to give 3 liter of 50% acetone extract.

Figure 31:
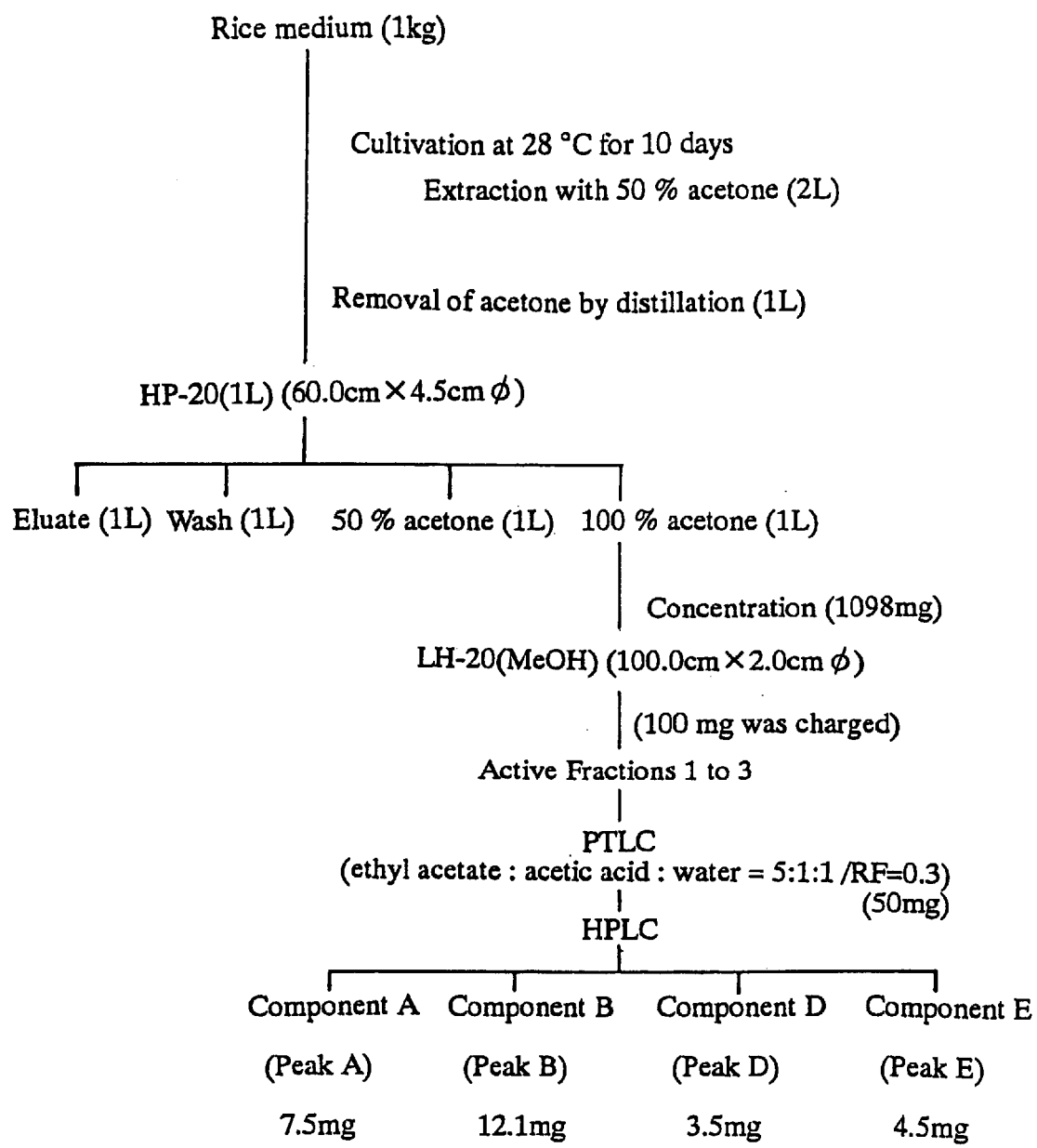
FIG. 31 is a scheme of purifying a cultivated extraction using a rice medium.

(Purification Method)
(1) Purification Method of Cultivated Extraction Using Medium A The acetone was distilled away from 2 liter of 50% acetone cultivated extraction using medium A (the resultant: 1 liter in total) and then the resultant was passed through and adsorbed onto a HP-20-Sephadex column (60.0 cm×4.5 cmφ). The column was washed with an equal volume of water, and the sample was eluted with an equal volume of 50% acetone and then with an equal volume of 100% acetone. The respective fractions were assayed against assay bacterium *Rhizoctonia solani* (AG-1IA), and it was thus confirmed that the active substances were eluted as the fraction eluted with 100% acetone. Then, 1 liter of the fraction eluted with 100% acetone was concentrated to give 1098 mg crude extract, and 100 mg of this crude extract was applied onto an LH-20 column (100.0 cm×2.0 cmφ) with methanol as a developing solvent. Each fraction was assayed, and the active fractions were thus confirmed. These active fractions were recovered and developed with silica gel TLC (ethyl acetate: acetic acid:water=5:1:1) and subjected to coloration reaction with sulfate molybdenum, whereby spots with Rf=about 0.3 were detected. These spots were not detected in the inactive fractions. From this result, it was estimated that the active substances are detected as spots with Rf=about 0.3, from which the active substances were further purified. The sample was developed on silica gel PTLC (ethyl acetate:acetic acid:water=5:1:1), scratched off, extracted with methanol, and isolated and purified by HPLC. The isolated and purified products were identified by instrumental analysis (FIG. 31).

(2) Isolation and Purification Method of Cultivated Extraction Using Medium BI

Figure 32:
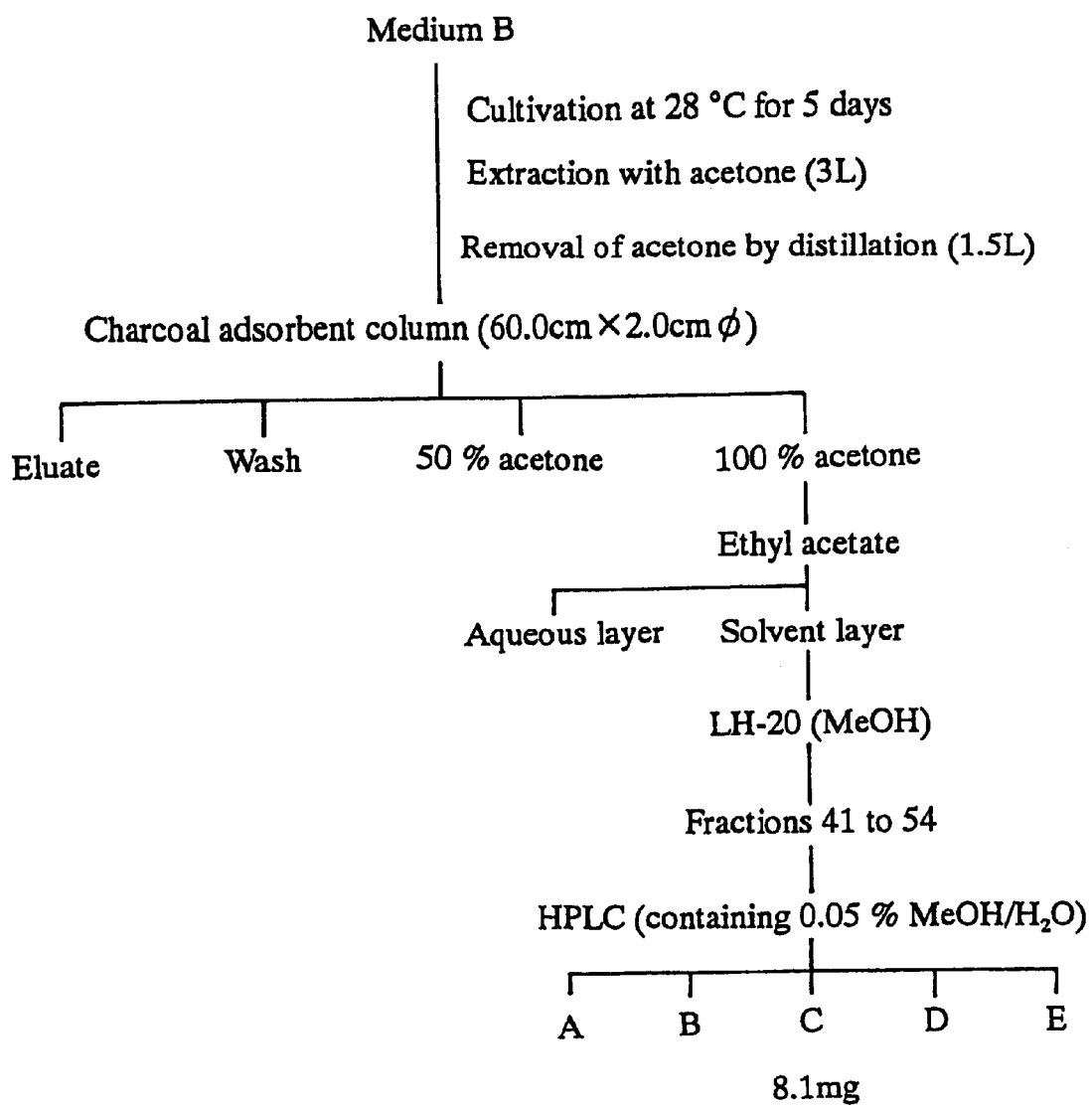
FIG. 32 is a scheme of purifying a cultivated extraction using medium BI.

The acetone was distilled away from 3 liter of 50% acetone cultivated extraction using medium BI (the resultant: 1.5 liter in total), and then the resultant was passed through and adsorbed onto an charcoal adsorbent column (60.0 cm×2.0 cmφ). The column was washed with an equal volume of water, and the sample was eluted with an equal volume of 50% acetone and then with an equal volume of 100% acetone. As a result of assaying each fraction with the assay bacterium *Staphylococcus aureus* 209P, it was confirmed that the active substances were eluted as the fractions eluted with 100% acetone. 1.5 liter of the fractions eluted with 100% acetone were concentrated, extracted by partition with ethyl acetate, applied to an LH-20 column with methanol as a developing solvent, and isolated and purified by HPLC. The isolated and purified products were identified by instrumental analysis (FIG. 32).

(Bioassay of the Isolated and Purified Products)
(1) Evaluation of the Isolated and Purified Products Using Medium A
Bioassay of the 4 Components A medium composed of 1.3% PDA (Nissui) and 0.002% chloramphenicol was used as the assay medium. The tips of hyphae of *Rhizoctonia solani* (AG-1IA) were bored by a cork borer and placed in the middle of the plate medium, and a paper disk impregnated with the isolated substances was placed at the side of the plate medium, and elongation of the hyphae was observed.

(2) Evaluation of the Isolated and Purified Product Using Medium BI
Bioassay of Component C (MW168)

The isolated and purified component C (MW: 168) is a novel material and maintains a very simple structure. Because component C was interesting as nucleus in cyclic compounds, bioassay of component C was conducted.

(3) Evaluation of the Products Against Bacteria
Bioassay

An agar medium containing a test bacterium was placed in a Petri dish and fixed therein. A paper disk containing the sample was placed thereon and incubated at 37° C. for 18 hours, and formation of a circle of inhibited growth was confirmed.

(a) Used Strains
The following 4 strains were used: *Staphylococcus aureus* 209P, *Pseudomonas syringal*, *Xanthomonoas Campestris* pv. citri, and *Erwinia sp.*

(b) Used Medium
For pre-culture, a bouillon medium (DIFCO) was used, and after overnight cultivation, the cultivation medium was diluted at ×$10^2$ and mixed with 0.5% upper-layer medium. As the medium for measuring the bacterium, Mycin agar (Mikumi Kagaku) was used.

Upper layer–1.5% Mycin agar (Mikuni Kagaku)+0.5% Mycin agar mixed with the overnight cultivation (diluted at ×$10^2$) in 2% bouillon medium (DIFCO)
Lower layer–2.0% Mycin agar (Mikuni Kagaku)

(c) Measurement of Antimicrobial Properties
A paper disk was impregnated with the isolated and purified product prepared at 1000 ppm, 500 ppm and 250 ppm respectively was air-dried, placed on the Petri dish and incubated at 37° C. for 18 hours, and whether a circle of inhibited growth was formed or not was observed.

(4) Measurement of Antimicrobial Properties (Minimum Inhibitory Concentration (MIC)) Against Staphylococcus (a) Used Strains
22 strains in total, that is, 1 strain of *S. aureus* 209P JC-1, 20 strains of 1G-stored, clinically separated Staphylococcus (10 strains each of MSSA and MRSA), and 1 strain of *E. coli* NIHJ JC-2 as the standard strain.

(b) Used Antimicrobial Chemicals

MW:168, methicilin (DMPPC, staphciliIn for injection, Lot. No. FSB 19,000 µg/mg, Banyu Pharmaceutical Co., Ltd.), vancomycin (VCM, Lot. No. 41H0457, 10750, SIGMA).

(c) Used Mediums

Mueller-Hinton agar (MIA, Difco) was used for measurement of antimicrobial properties, and Mueller Hinton broth (MHB, Difco) was used for pre-cultivation.

(d) Measurement of Antimicrobial Properties

The minimum inhibitory concentration (MIC) of each chemical against the used strain was determined according to an agar plate dilution method in accordance with the standard methods of Japanese Society of Chemotherapy. The strain was sprayed onto MHA and cultured at 37° C. overnight, and the resultant colonies were cultured in MHB at 37° C. overnight, and its microbial liquid was diluted 100-fold (1000-fold dilution for E. coli) and used as inoculation liquid.

(Results)

(1) Result of the Assay Bacteria

The activities in the cultivation extracts from mediums A and BI respectively are shown in Table 2.

The antimicrobial spectrum was determined using the following assay bacteria.

TABLE 2

| | Division | |
|---|---|---|
| Used microorganisms | Medium A | Medium BI |
| Botrytis cinema | − | − |
| Rhizoctonia solani (AG-1IA) | + | − |
| Bacillus subtilis ATCC6633 | + | + |
| Micrococcus luters ATCC6633 | + | + |
| Staphloccocus aureus 209P | + | + |
| Escherichia coli NIHJ | − | + |
| Saccharomyces cerevisiae SHY3 | − | − |
| Candida albicans M9001 | − | − |
| Candida pseudotropicalis M9035 | − | − |
| Cryptococcus neoformans M9010 | − | − |
| Debaryomyces hansenii M9011 | − | − |
| Trigonopsis variabilis M9031 | − | − |
| Schizosaccharomyces pombe M9025 | − | − |
| Hansenula schneggi IAM4269 | − | − |

As a result of assaying the cultivated extraction using medium A, hyphae of Rhizoctonia solani (AG-1IA) were observed to be kept away from the paper disk impregnated with the cultivated extraction using medium A. It was estimated that growth of the hyphae is inhibited by the active substances in the culture produced by the present microorganism in medium A. Accordingly, we attempted to isolate and purify the active substances from the culture liquid from medium A by using their inhibitory action on Rhizoctonia solani (AG-1IA) as the indicator.

As a result of assaying the cultivated extraction using medium BI, the activity against Botrytis cinerea and Rhizoctonia solani could not be confirmed, and formation of a circle of inhibited growth of bacteria only was confirmed. This suggests that the present microorganism has antimicrobial activity other than the antagonistic action, and produces an antibiotic. In particular, the circle of inhibited growth of Staphylococcus aureus 209P was clear, and thus we attempted to isolate and purify the antibiotic from medium BI by using its inhibitory action on bacterium Staphylococcus aureus 209P as the indicator. The antimicrobial spectrum of the culture in medium A is different from that of the culture in medium BI, thus suggesting that the present microorganism produces different kinds of active substances. Accordingly, we determined to isolate and purify the respective active substances.

(2) Results of Cultivation (a) Result of Cultivation Using Medium A

The present microorganism was subjected to stationary cultivation at 28° C. for 10 days in ten 500-ml Erlenmeyer flasks each containing medium A (rice medium, 1 kg), to give 2 L cultivation extracted with 50% acetone.

(b) Examination of Medium B and Result of Cultivation

The activity of the present microorganism was recognized in mediums BI and BII shown in Table 1, and the present microorganism whose stronger activity was recognized in medium BI was confirmed to produce the active substances under conditions with a smaller amount of the nitrogen source. From this result, medium BI was used in shake cultivation at 28° C. for 5 days.

Figure 2:
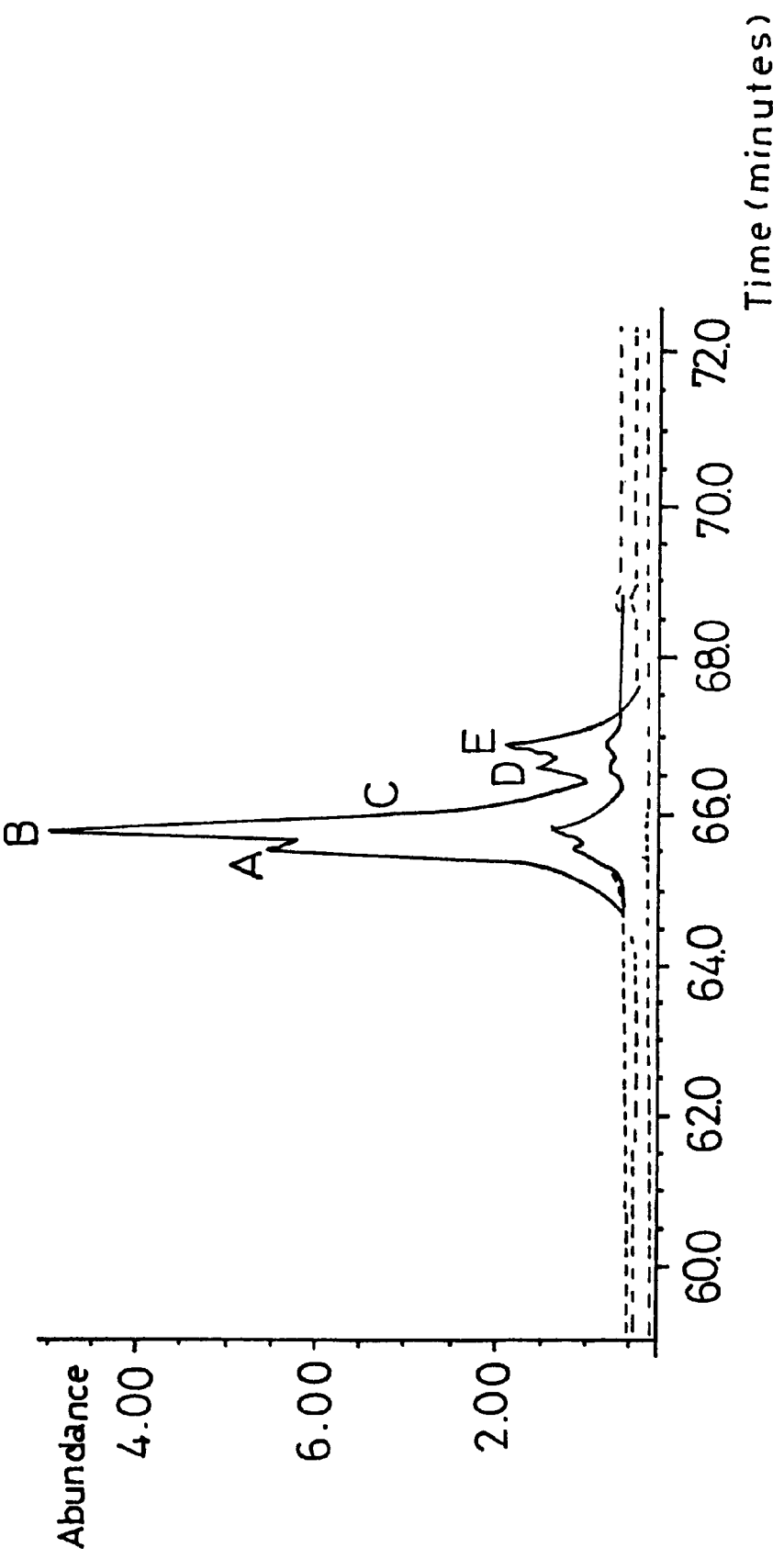
FIG. 2 is an enlargement of FIG. 1.
Figure 3:
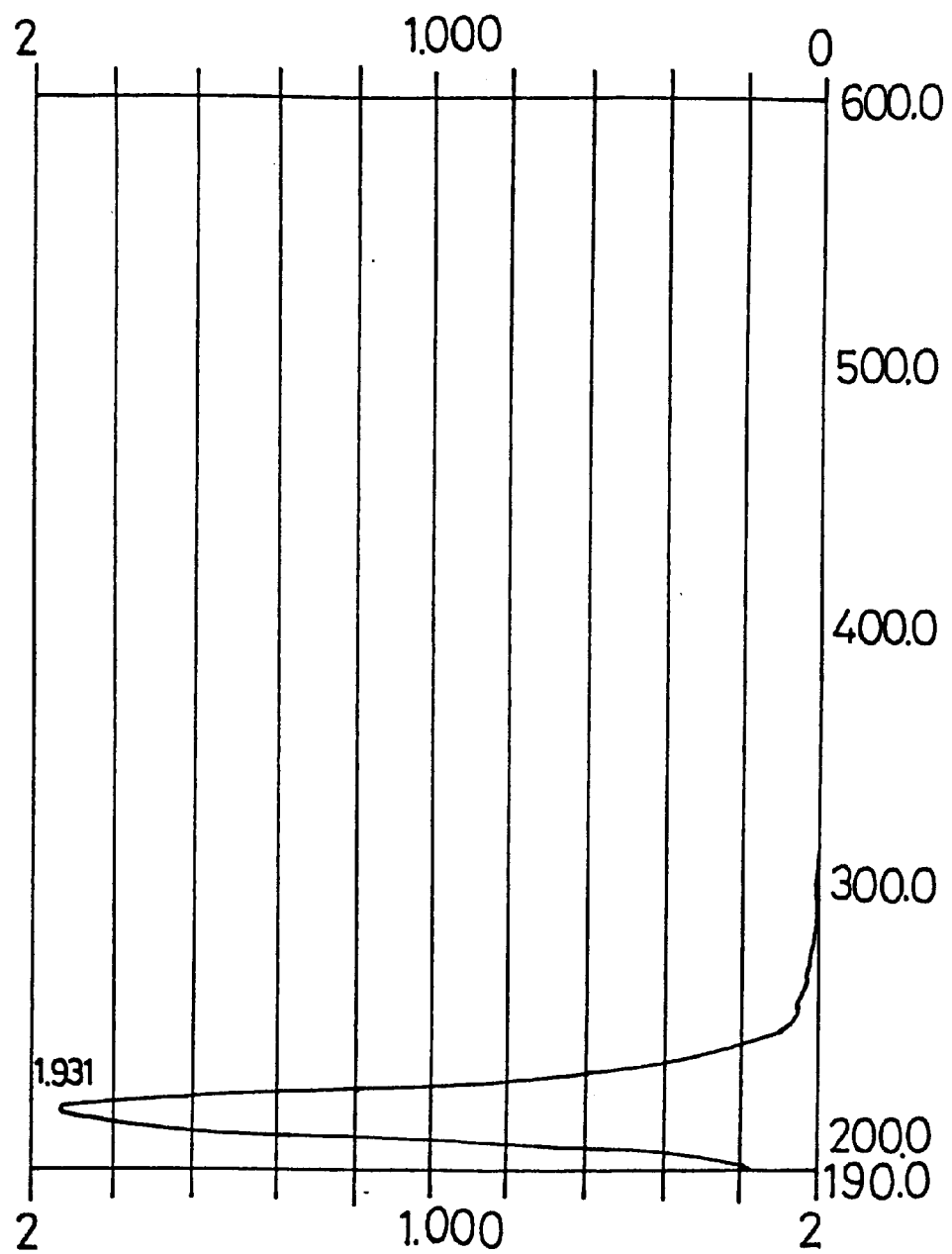
FIG. 3 shows the UV absorption of component A.
Figure 4:
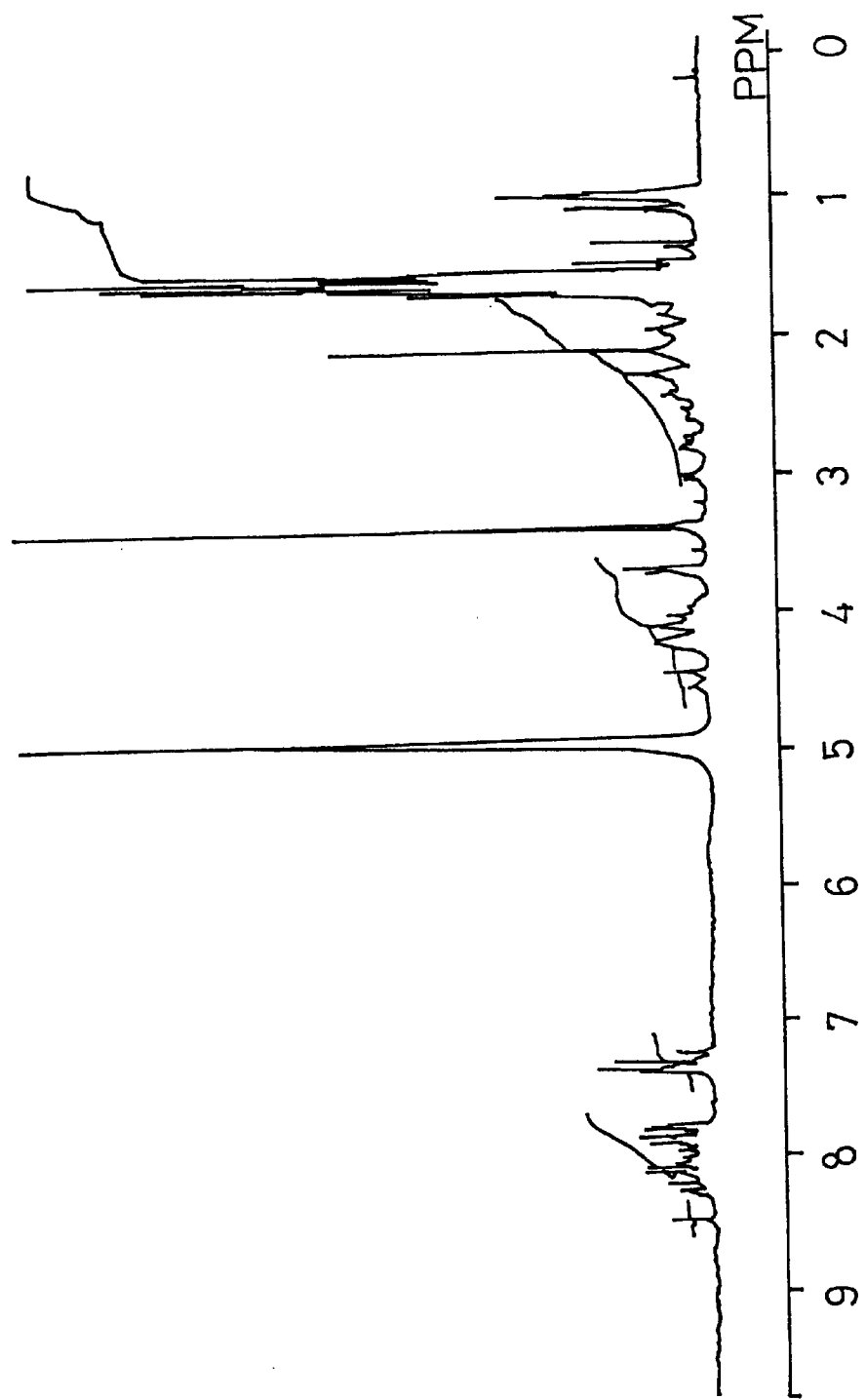
FIG. 4 is a $^1$H-NMR profile (CD$_3$OD) of component A.
Figure 6:
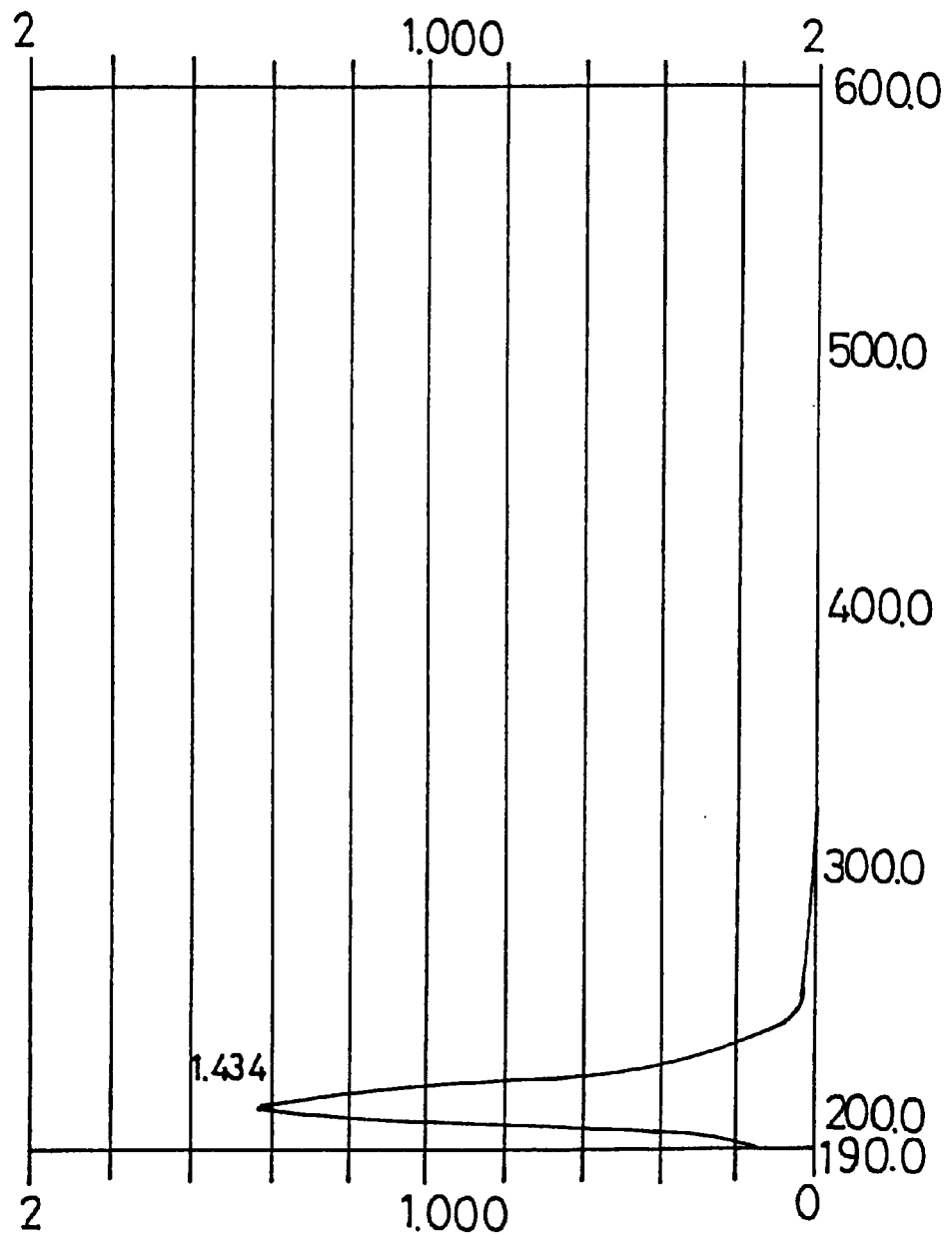
FIG. 6 shows the UV absorption of component B.
Figure 7:
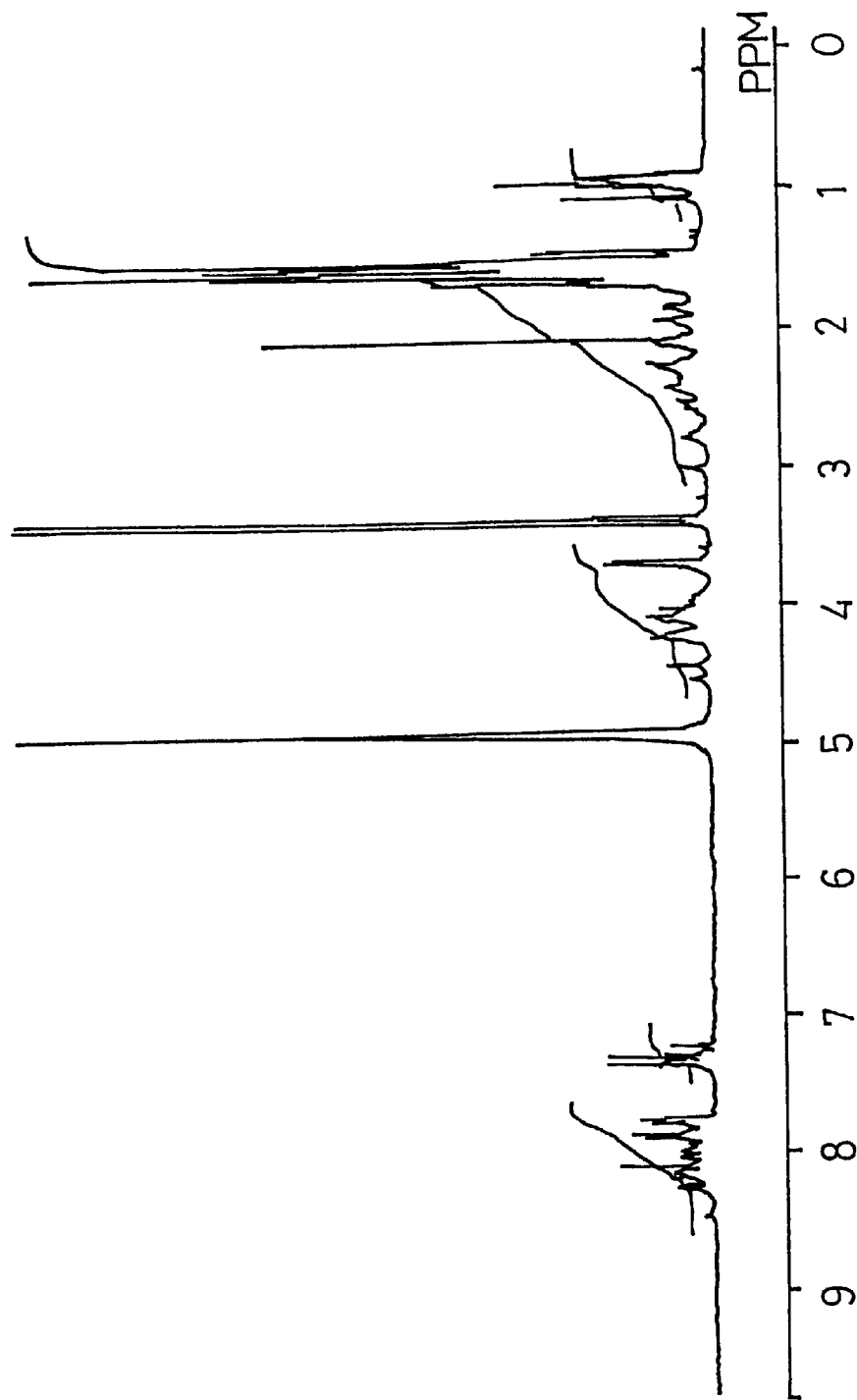
FIG. 7 is a $^1$H-NMR profile of component B.
Figure 9:
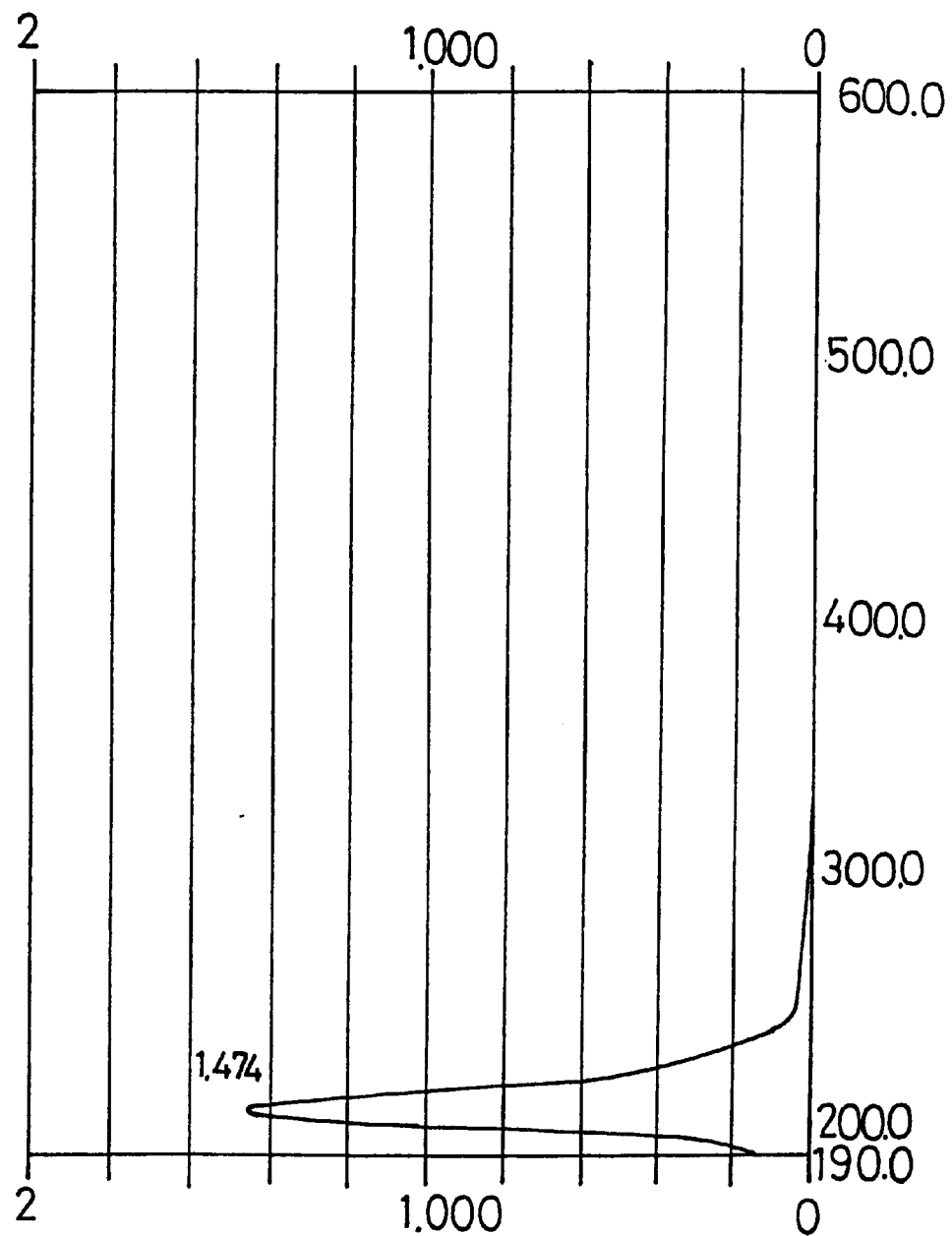
FIG. 9 shows the UV absorption of component D.
Figure 10:
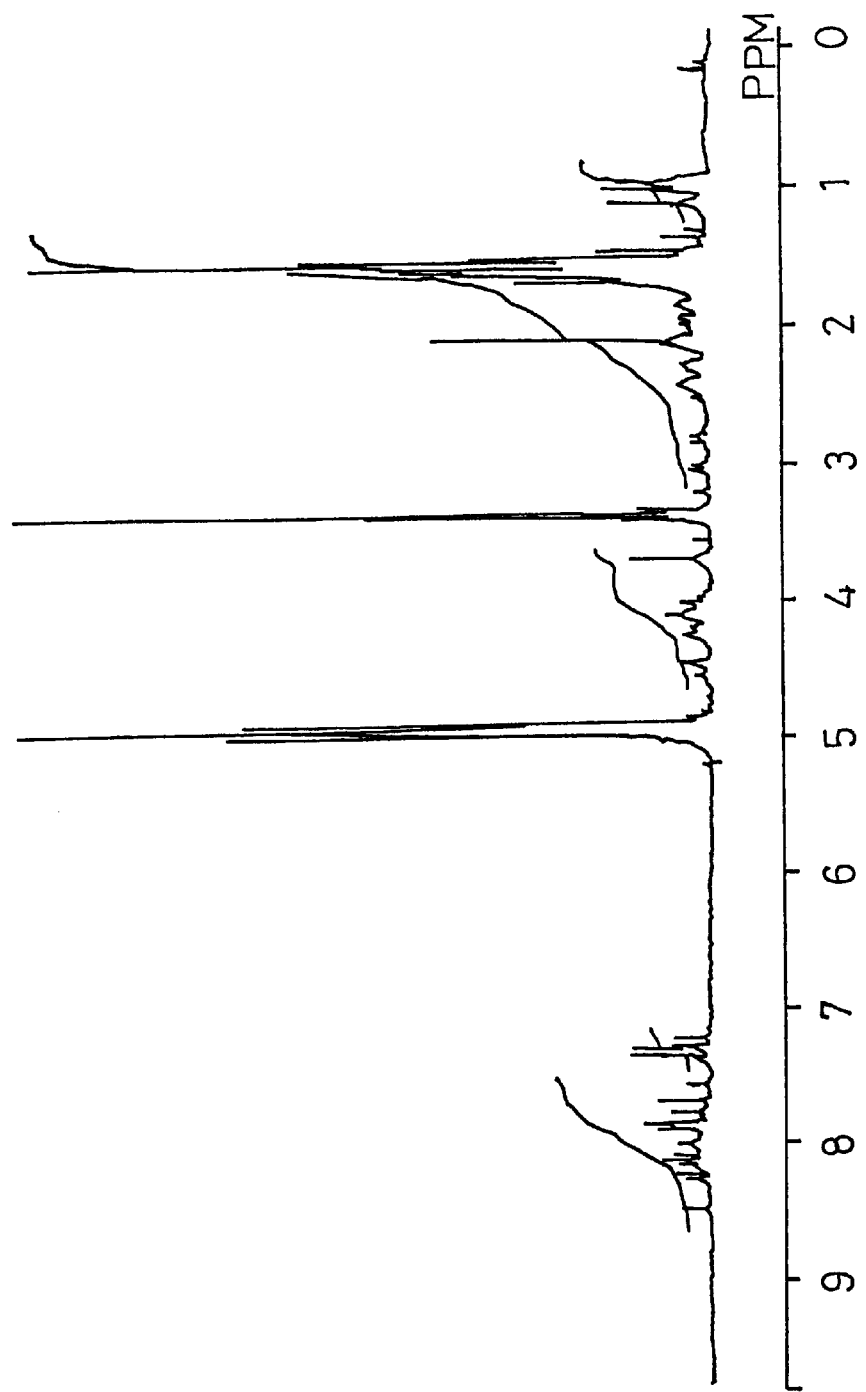
FIG. 10 is a $^1$H-NMR profile of component D.
Figure 11:
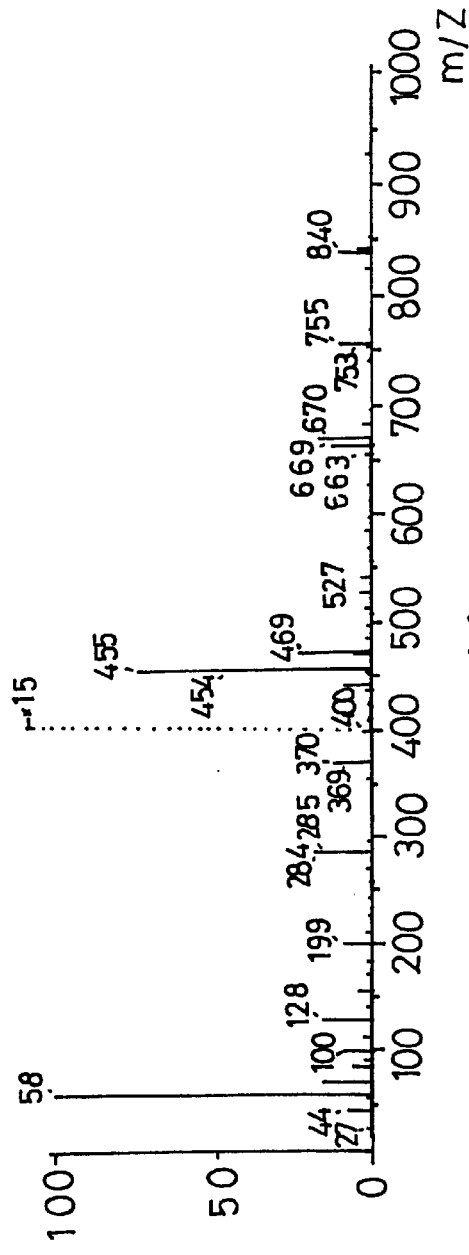
FIG. 11(*a*) and (*b*) show mass spectrometry of component D.
Figure 11:
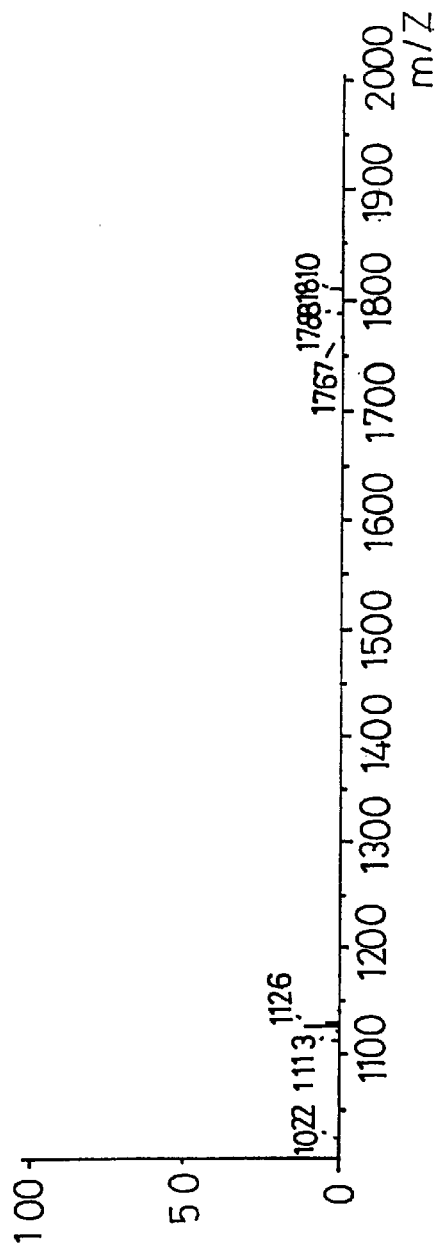
Figure 12:
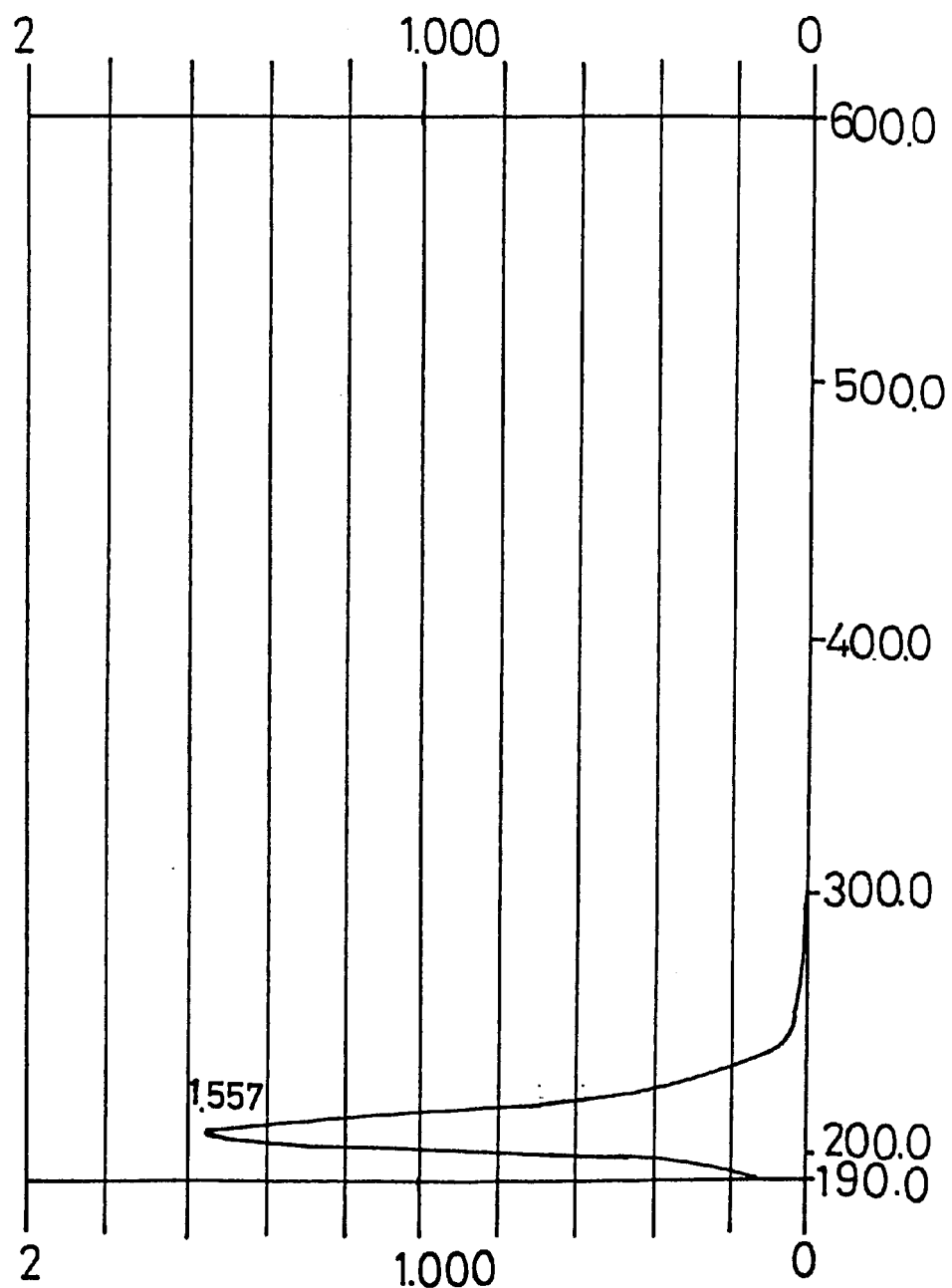
FIG. 12 shows the UV absorption of component E.
Figure 13:
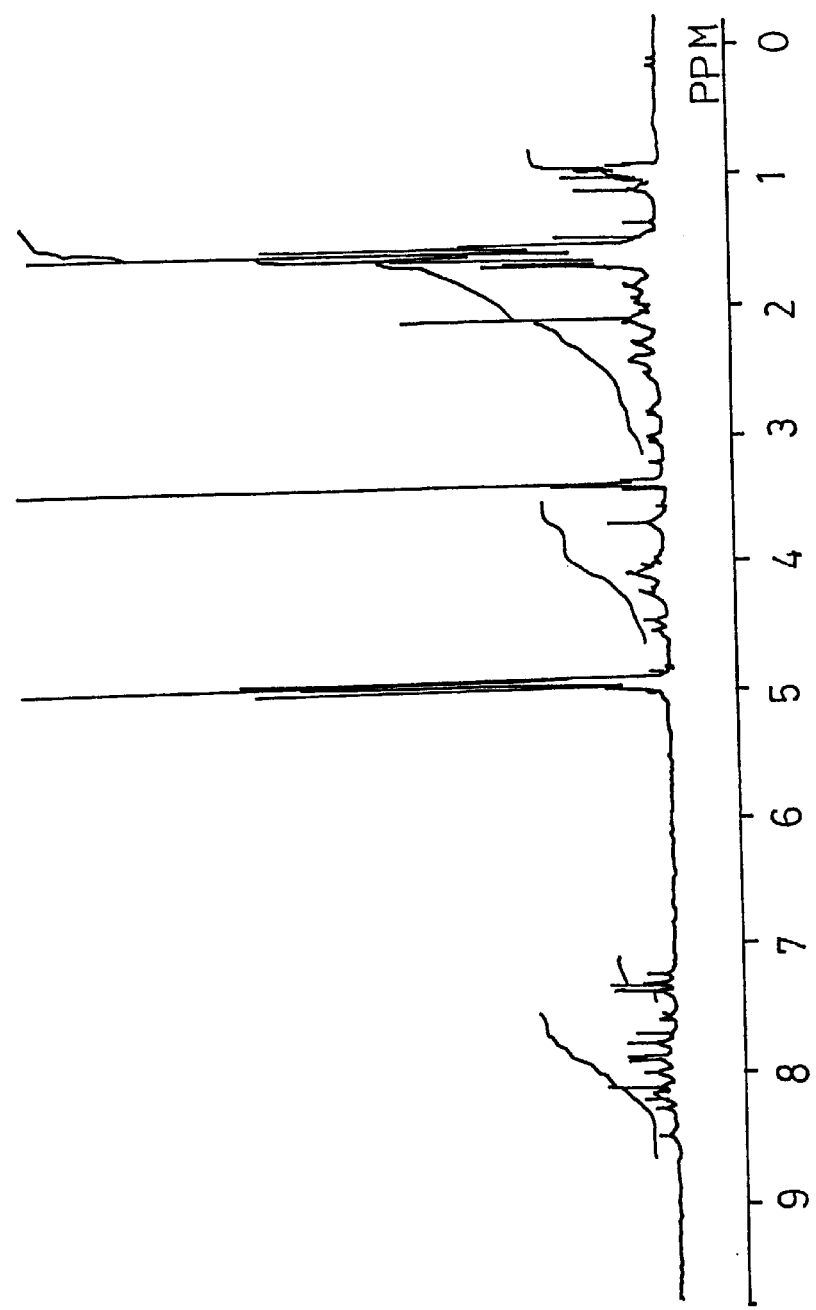
FIG. 13 is a $^1$H-NMR profile of component E.
Figure 14:
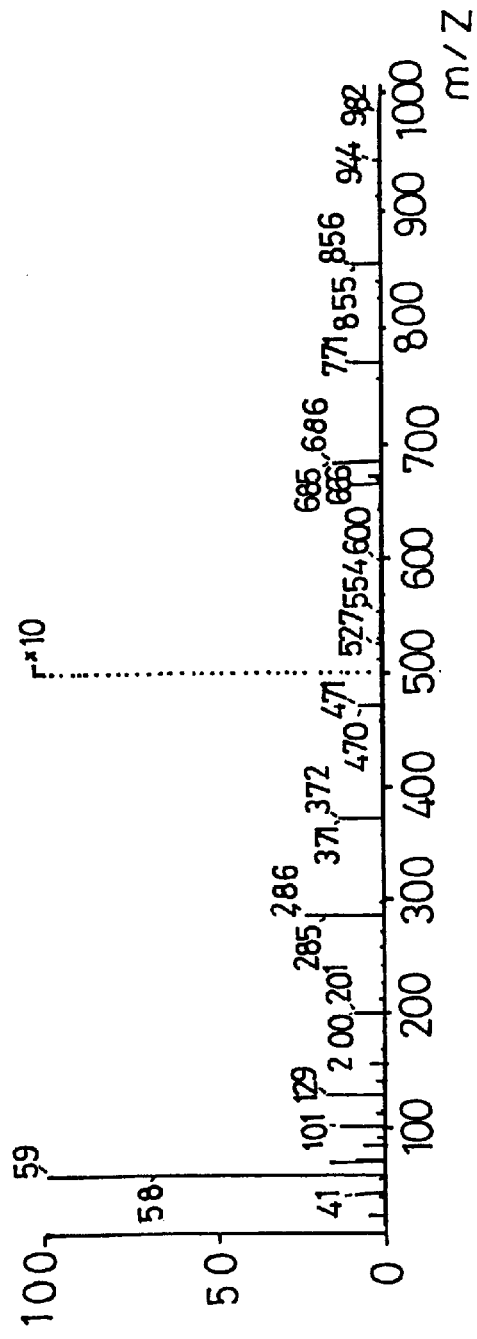
FIG. 14(*a*) and (*b*) show mass spectrometry of component E.
Figure 14:
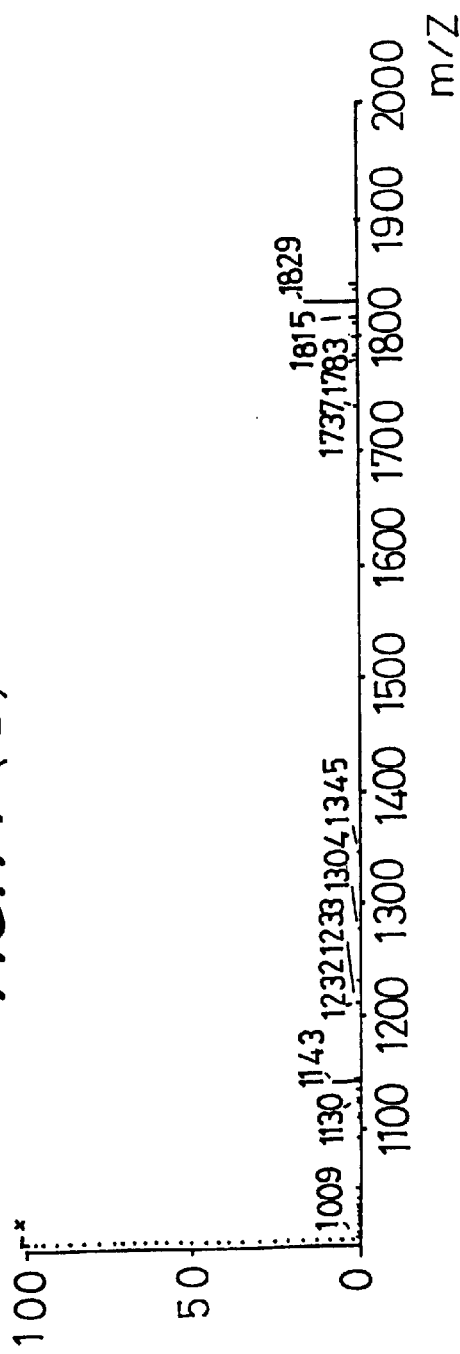

(3) Results of Purification (a) Result of Purification of the Cultivation Using Medium A Using the crude product obtained as active fractions in silica gel PTLC, its purity was confirmed by HPLC (MeOH/$H_2O$ containing 0.05% TFA). In this analysis, the crude product was analyzed at a flow rate of 1 ml/min. with 0 to 100% gradient in 0 to 30 minutes and then 100% methanol in 30 minutes and thereafter, and as a result the active substance was detected at a RT (retention time) of 32.5 minutes (Fr. 65) (FIG. 1). It seemed at first glance that a peak of the single substance was detected, but magnification of this peak revealed some peaks (FIG. 2). Compounds in these peaks were referred to as A, B, C, D and E in the order of increasing RT (FIG. 2), among which 4 components were isolated and purified. The isolated and purified components and the amounts thereof were as follows: component A, 7.2 mg; component B, 12.1 mg; component D, 3.5 mg; and component E, 4.5 mg. Because component C occurred in a very small amount, we gave up its purification.

(b) Result of Purification of the Cultivation Using Medium BI

By assaying the respective fractions, it was confirmed that fractions 41 to 54 were active and recovered. These fractions, fractionated and analyzed by HPLC (MeOH/$H_2O$, containing 0.05% TFA), were referred to as components A, B, C, D and E respectively in the order of increasing RT, and it was thus confirmed that the 5 components are present. Out of these components, 8.1 mg component C could be isolated and purified.

(4) Results of Instrumental Analysis (a) Isolated and Purified Products of Medium A From the results of UV absorption spectrum, mass spectrometry and NMR (FIGS. 3 to 14), it was judged that these components are polypeptides of peptibols type containing Aib (α-aminoisobutyric acid). A peptibols-type antibiotic is characterized in that it contains α-aminoisobutyric acid (Aib) in the amino acid sequence thereof, which is characterized in that the N-terminus is an acetyl group while the C-terminus is an amino alcohol linkage (terminating often at a phenylalaniol group). It was estimated by mass spectrometry that the purified products of this invention, that is, components A, B and D, have the following partial amino acid sequences, and these partial structures were compared with the amino acid sequences of existing peptibols, indicating that there is no agreement therebetween, thus suggesting that the present products are novel peptibols. Component E could not be judged because of difficult estimation of its amino acid sequence.

UV Absorption wavelength: The 4 components showed terminal absorption (FIGS. 3, 6, 9 and 12).

Component A = 1933 (FIG. 5)
Component B = 1949 or 1964 (FIG. 8)
Component D = 1810 (FIG. 11)
Component E = 1829 (FIG. 14)
Estimated structures:

Component A:   Ac-Aib-Ala-Aib-Aib-Aib-Aib-Gln-Aib-Aib- . . .
Component B:   Ac-Aib-Ala-Aib-Aib-Val-Aib-Gln-Aib-Aib- . . .
Component D:   Ac-Aib-Ala-Aib-Aib-Aib- . . .

(b) Active Substances of Medium BI (Liquid Medium)

Figure 15:
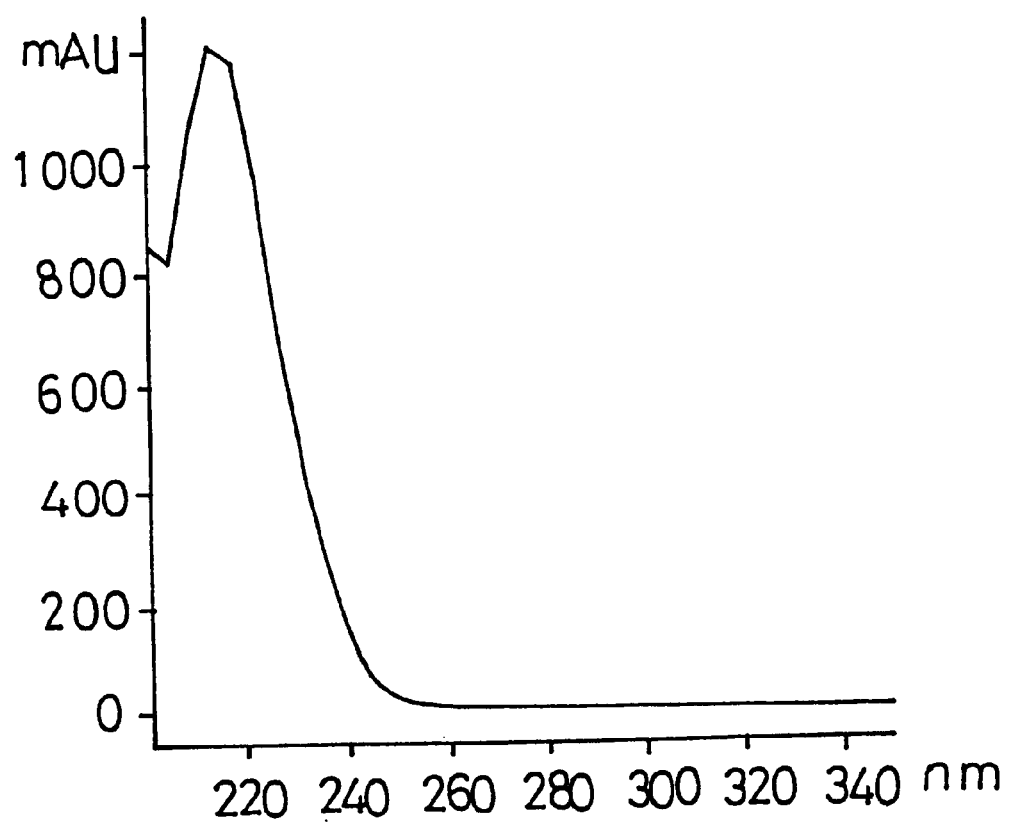
FIG. 15 shows the UV absorption of component A.
Figure 16:
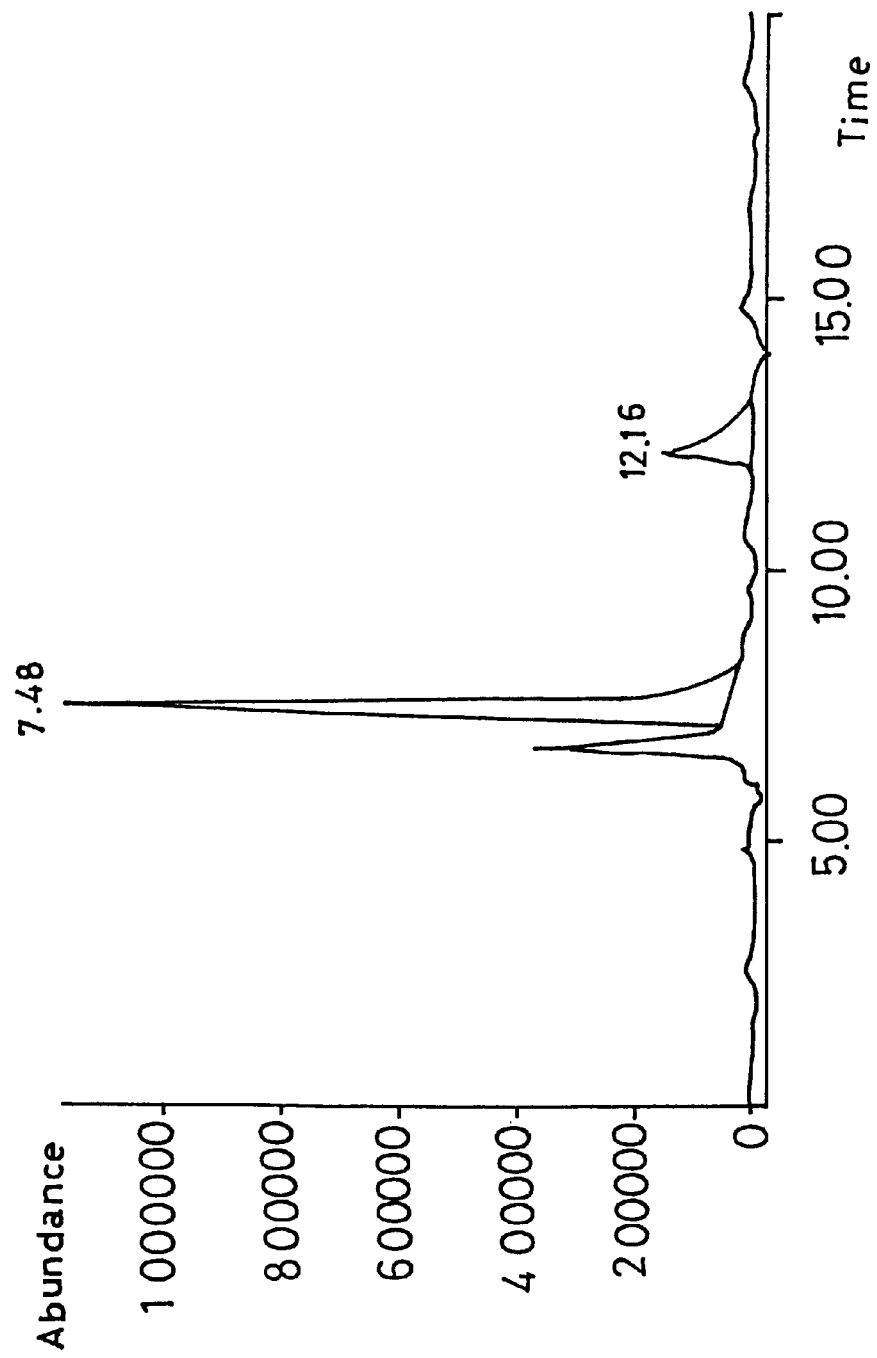
FIG. 16 is a HPLC profile of component A.
Figure 17:
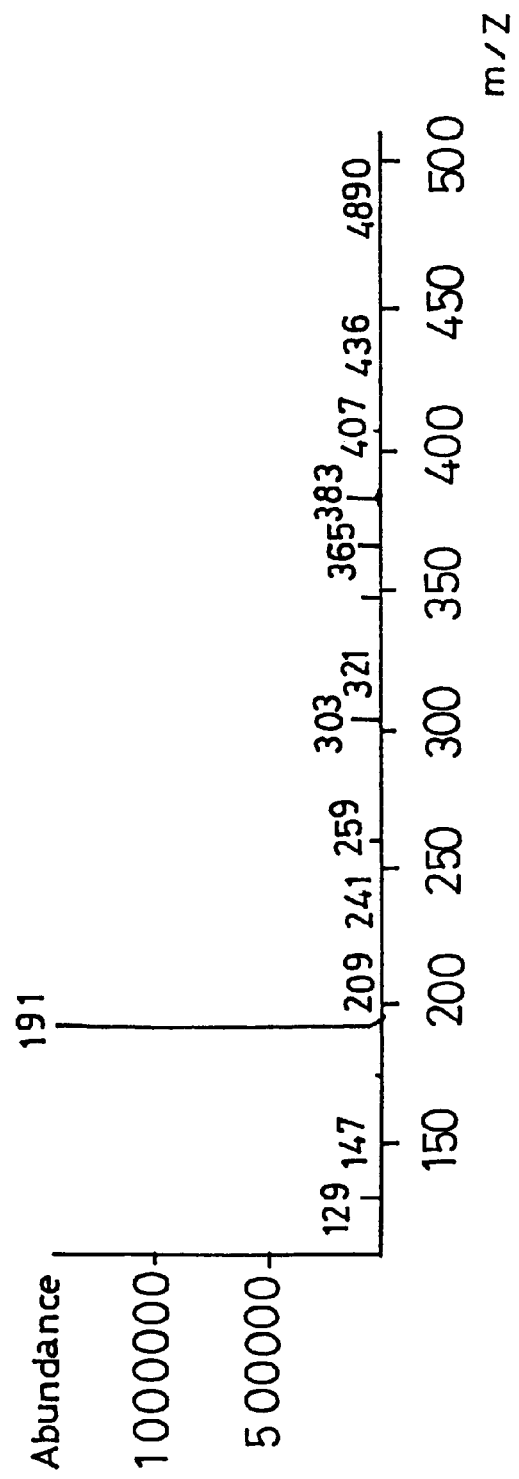
FIG. 17 shows mass spectrometry of peak A detected in FIG. 16.
Figure 18:
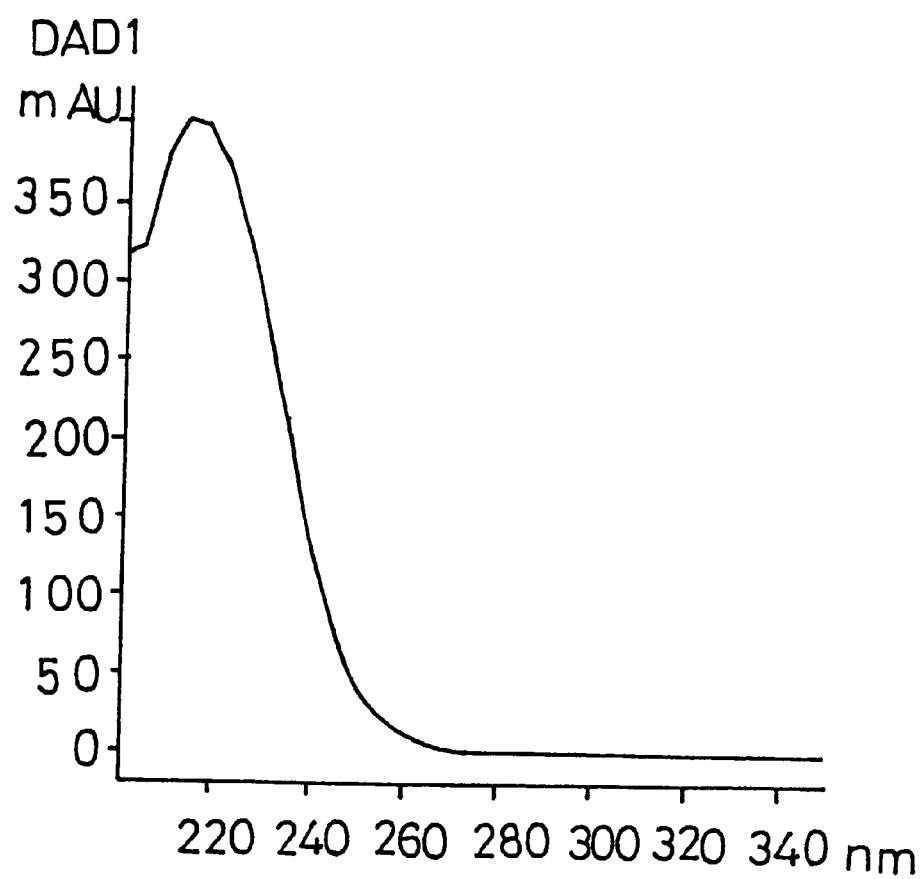
FIG. 18 shows the UV absorption of component B.
Figure 19:
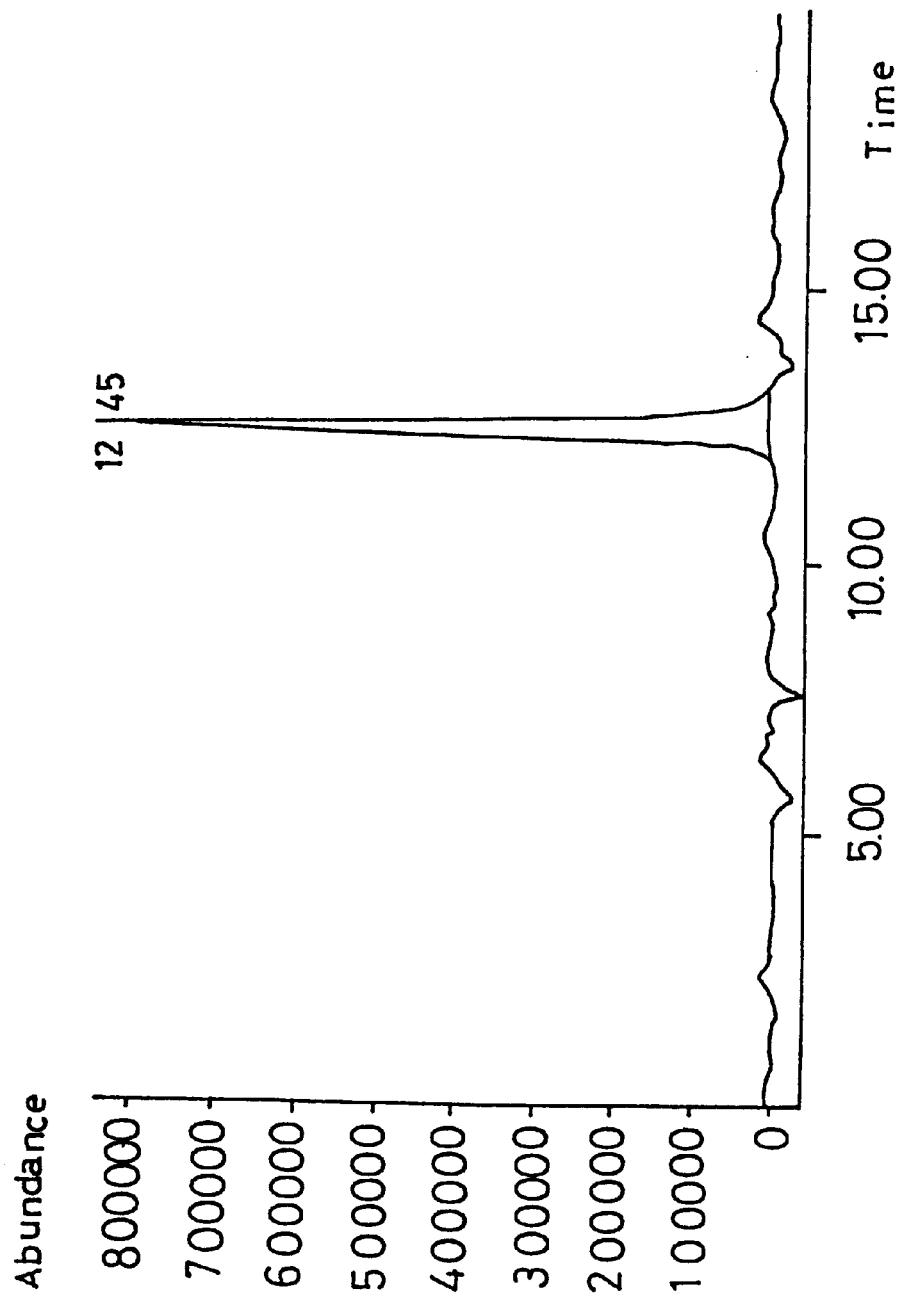
FIG. 19 is a HPLC profile of component B.
Figure 20:
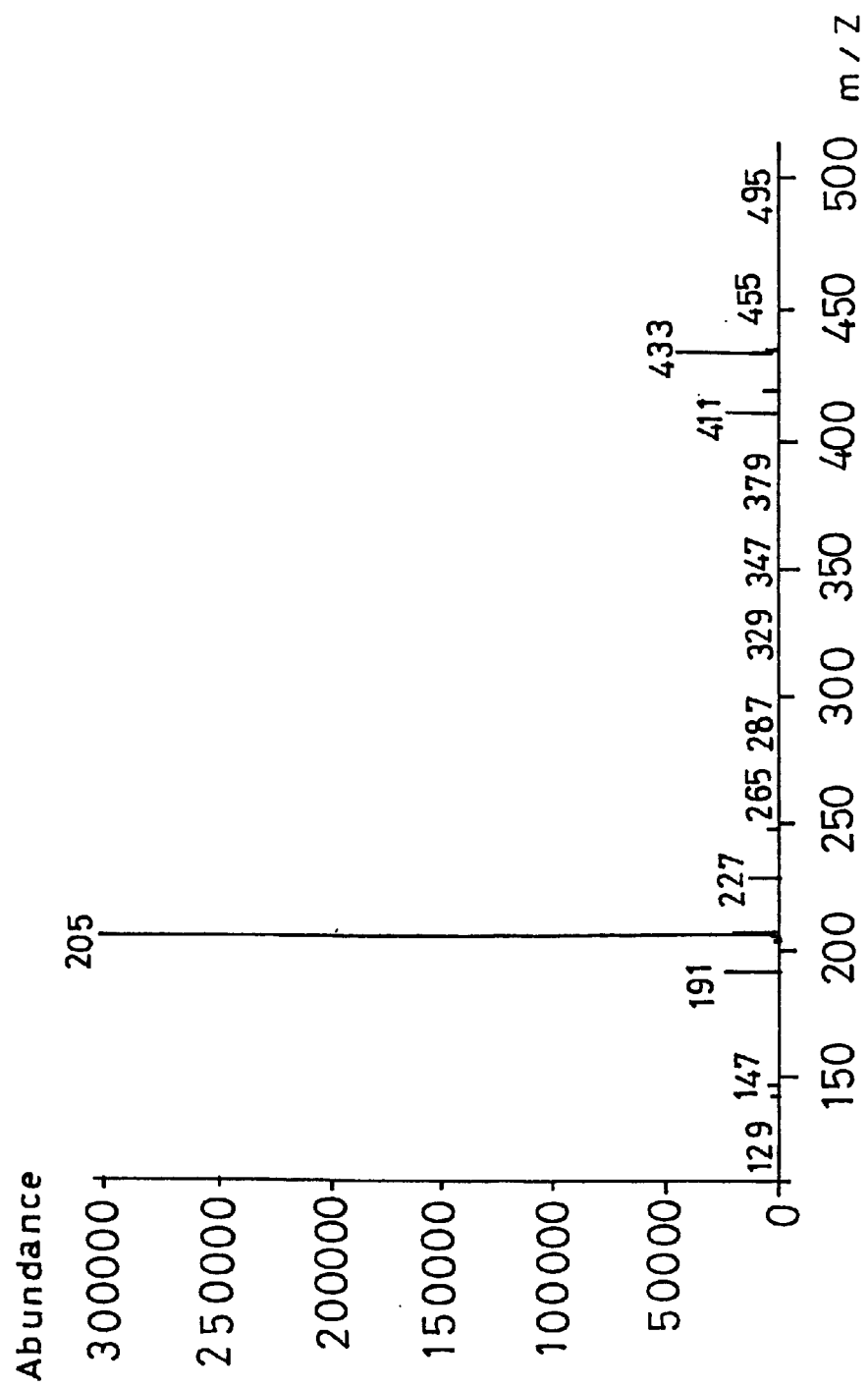
FIG. 20 shows mass spectrometry of peak A detected in FIG. 19.
Figure 21:
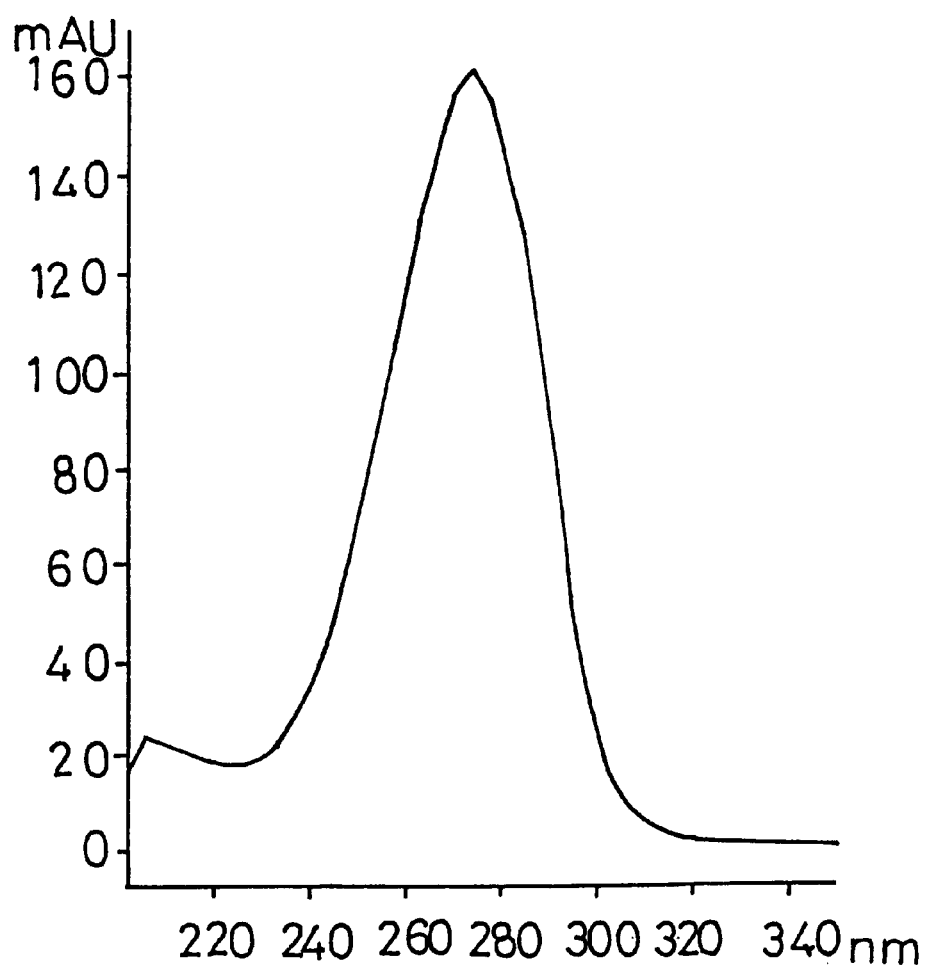
FIG. 21 shows the UV absorption of component C.
Figure 22:
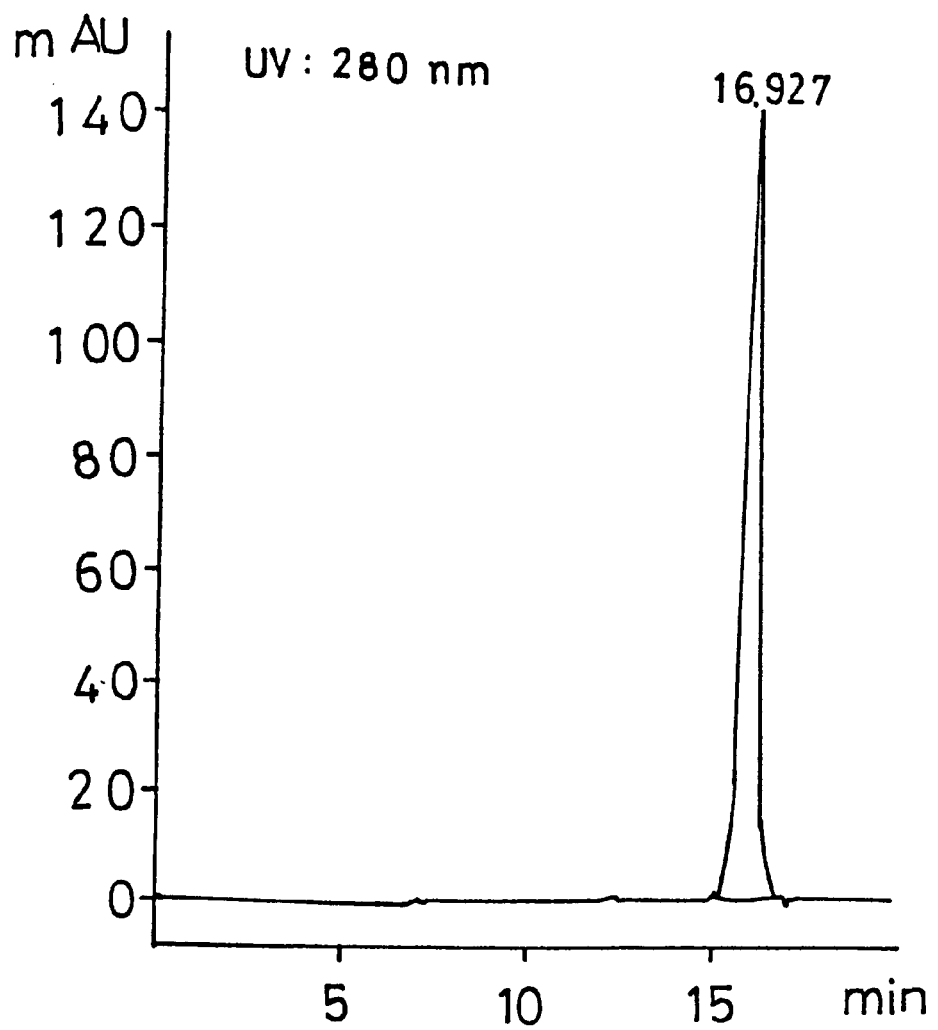
FIG. 22 is a HPLC profile of component C.
Figure 23:
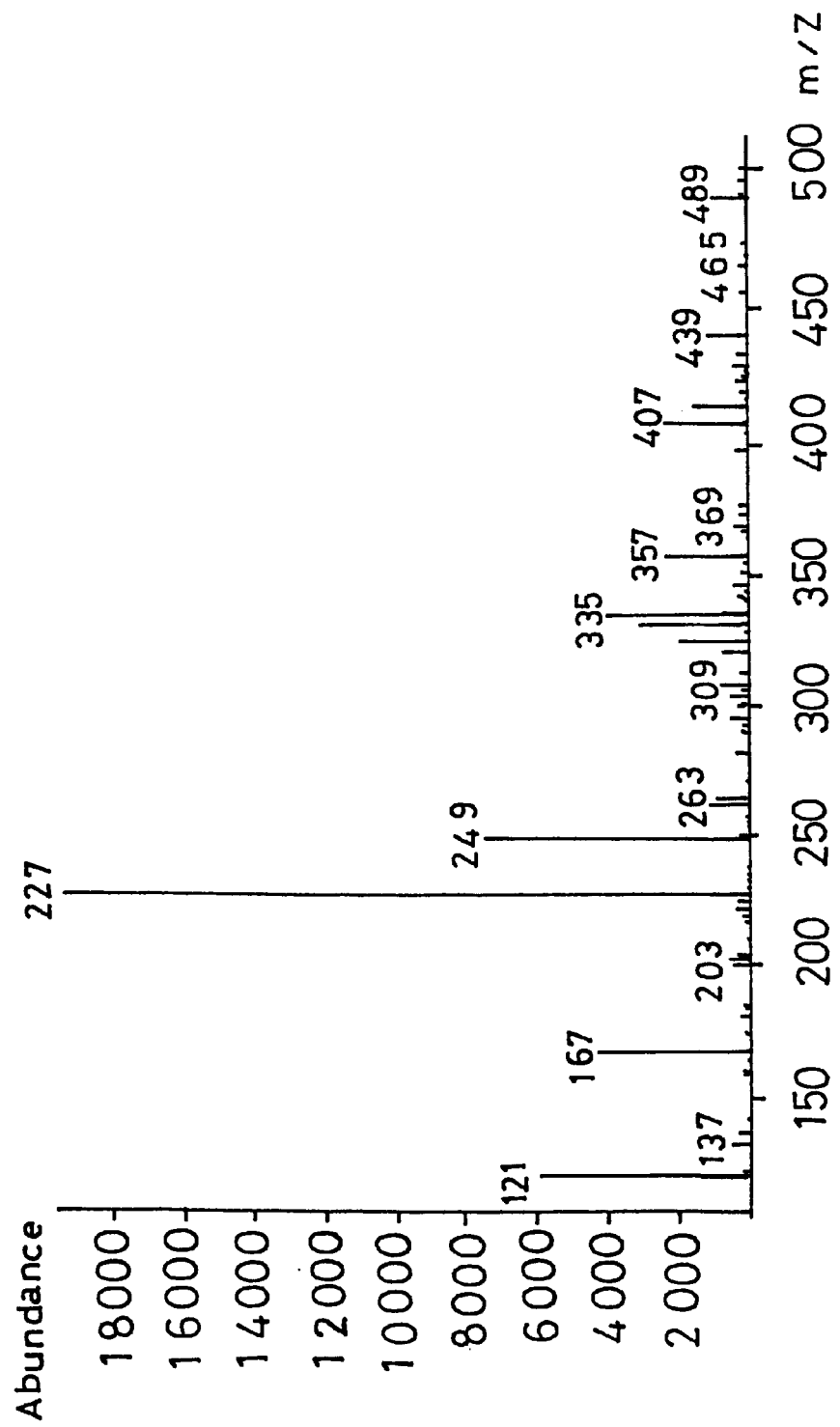
FIG. 23 shows mass spectrometry of peak A detected in FIG. 22.
Figure 24:
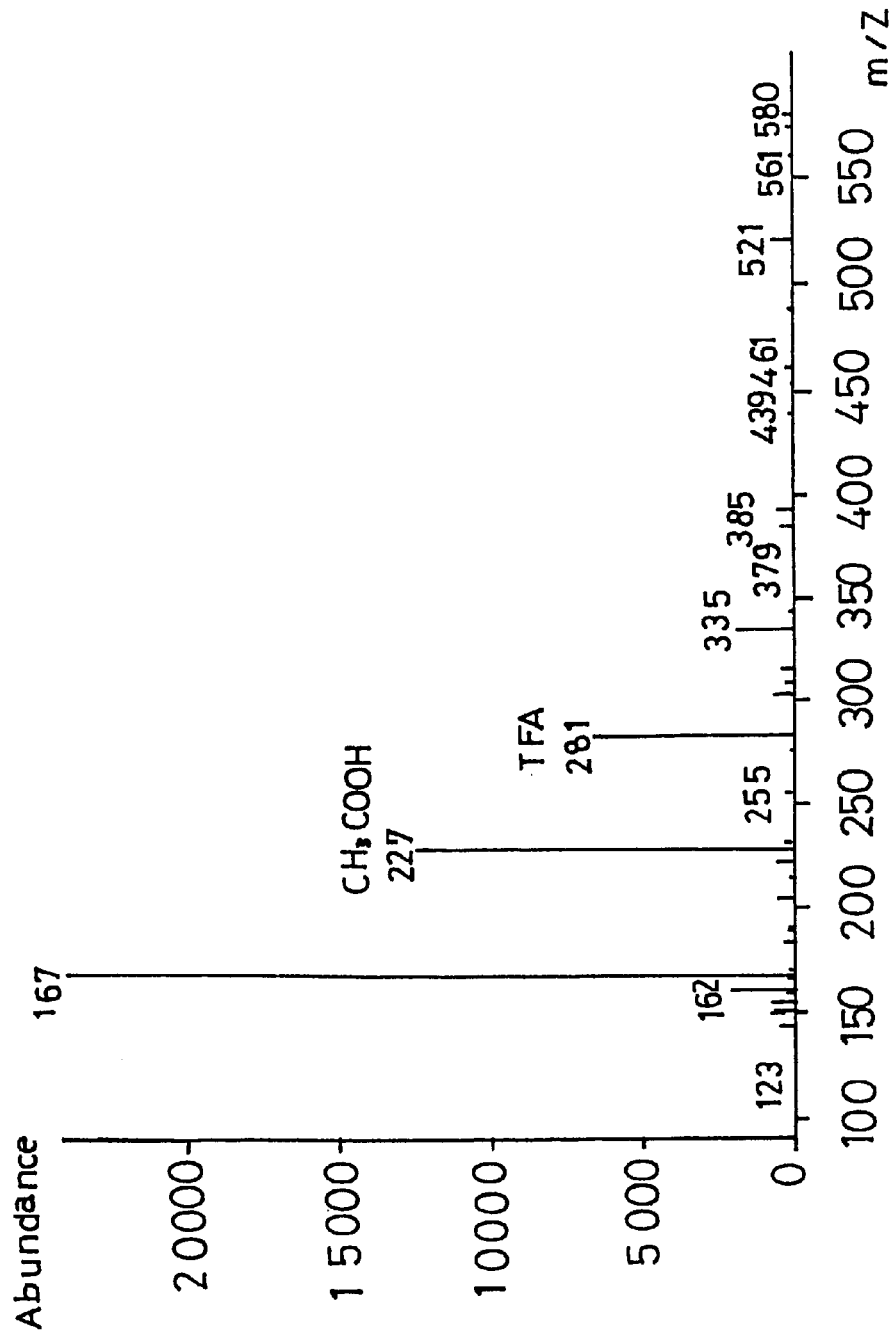
FIG. 24 shows mass spectrometry of component C.
Figure 25:
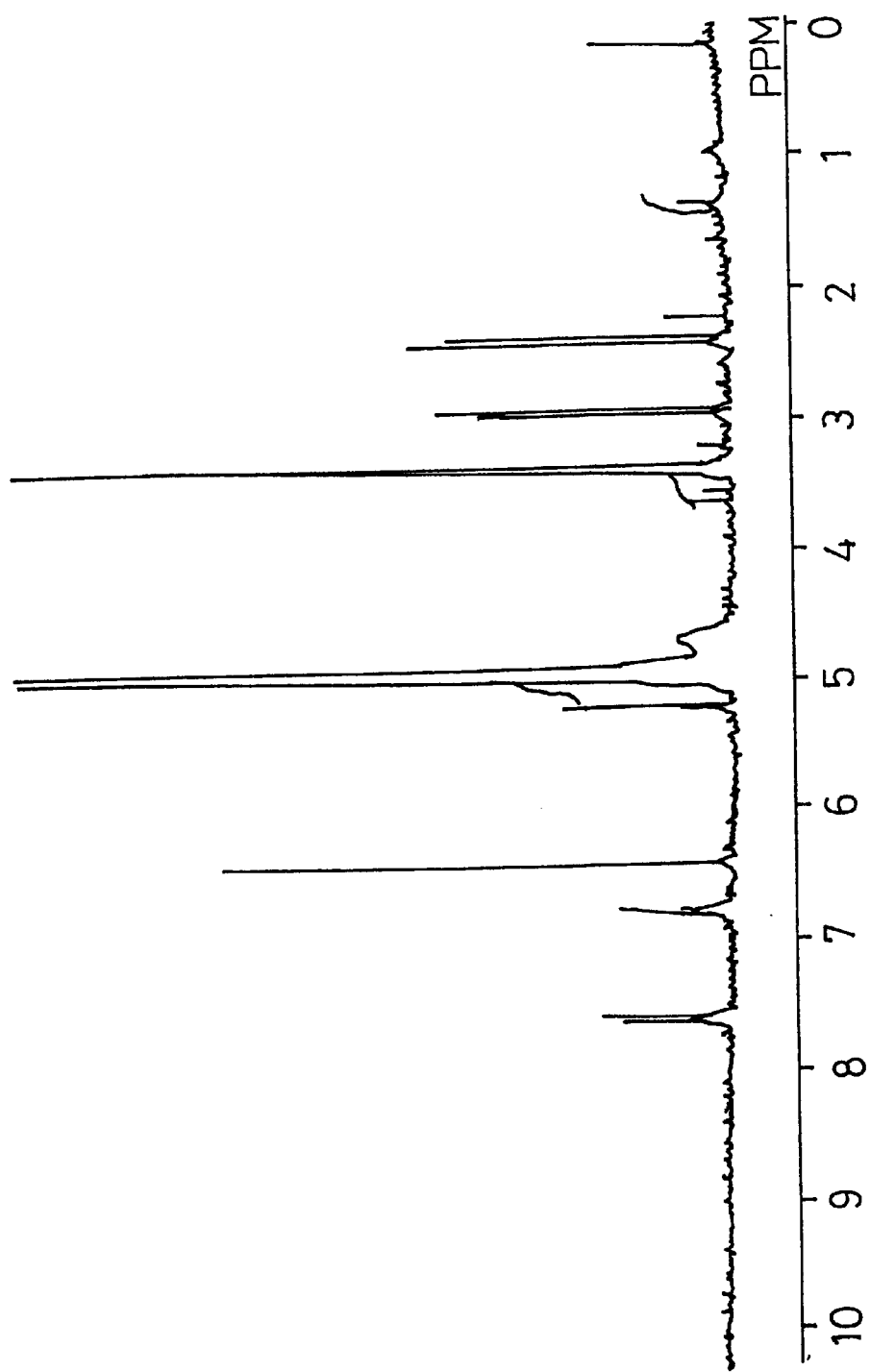
FIG. 25 is a $^1$H-NMR profile ($CD_3OD$) of a peak of component C.
Figure 26:
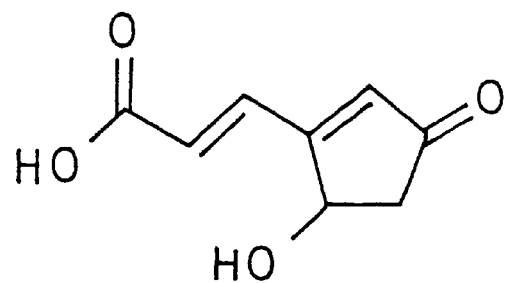
FIG. 26 shows the chemical structure of component C.
Figure 27:
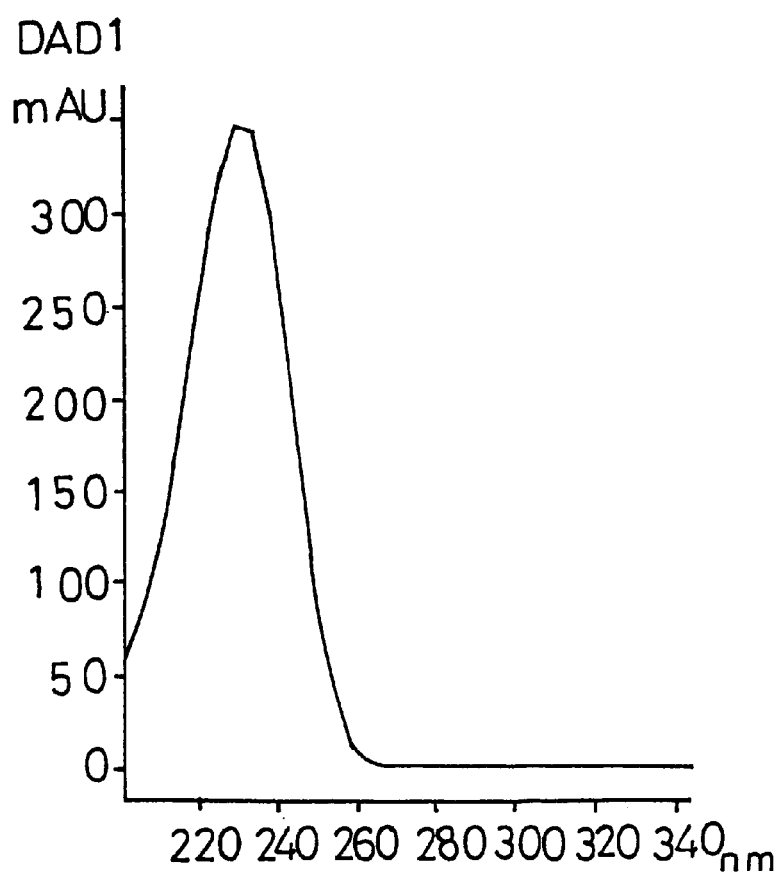
FIG. 27 shows the UV absorption of component D.
Figure 28:
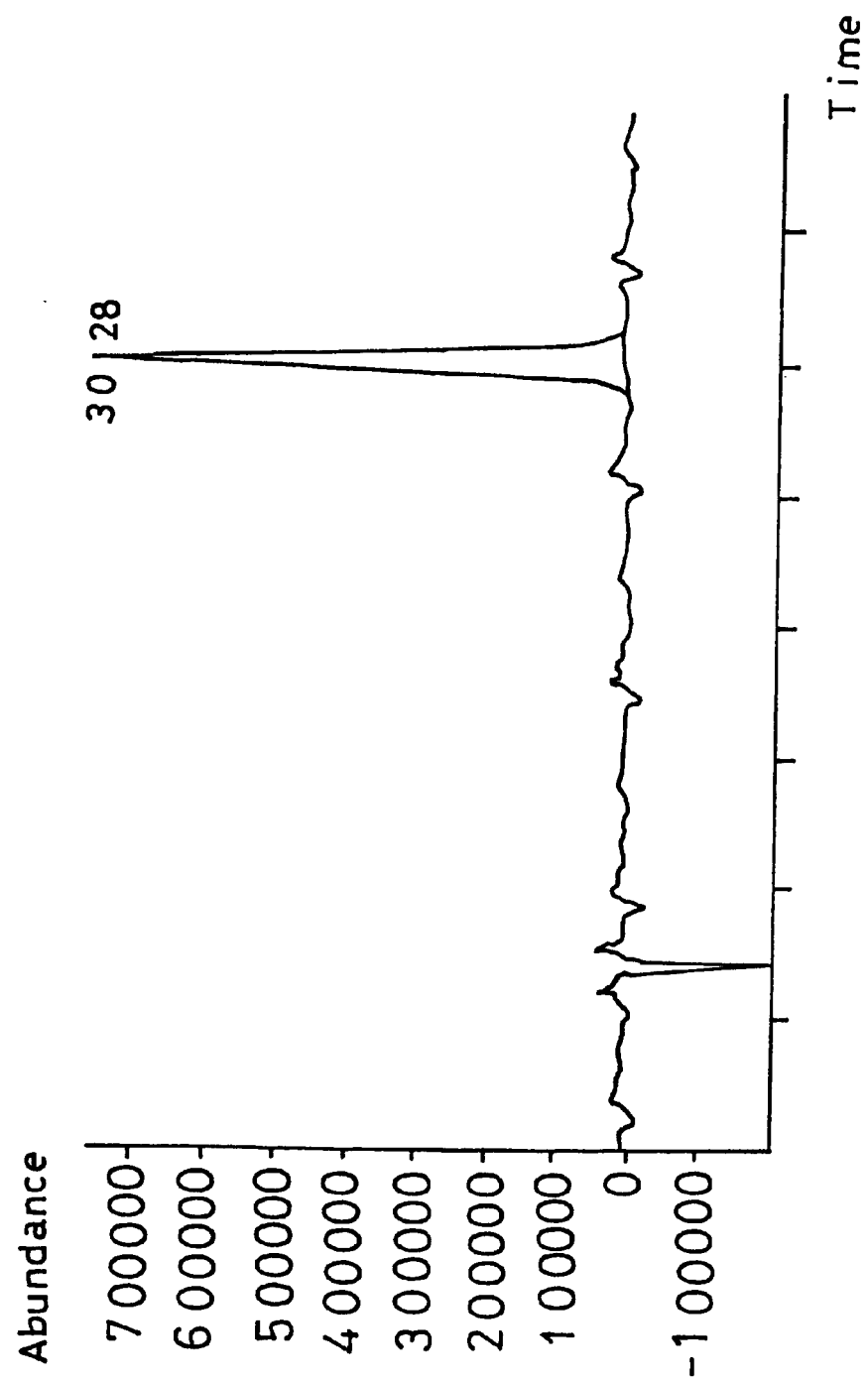
FIG. 28 is a HPLC profile of component D.

As a result of instrumental analysis, component C was estimated to be a novel substance having a molecular weight of 168 ($C_8H_8O_4$). Isolation and purification of the other components was very difficult and judged to be not feasible, but their LC/MS was conducted. The UV absorption of component A appeared at the terminal (FIG. 15). Using Capcel pac C18 UG120 (2×150 mm), HPLC was conducted with 1% acetic acid:acetonitrile=98:2 at a flow rate of 0.2 ml/min. at room temperature. Component A was detected at a RT of 7.48 minutes (FIG. 16). As a result of mass spectrometry of the fraction in which component A was detected, its molecular weight was estimated to be 192 (FIG. 17). Component B was also analyzed in analogous manner, indicating that component B showed UV absorption at the terminal (FIG. 18), and was detected at a RT of 12.45 minutes in HPLC (FIG. 19). As a result of mass spectrometry, its molecular weight was estimated to be 206 (FIG. 20). Component C is a fraction that could be successfully isolated and purified. Component C had UV absorption at a wavelength of 270 nm (FIG. 21), and was detected at a RT of 15.92 minutes in HPLC (FIG. 22). As a result of mass spectrometry, its molecular weight was estimated to be 168 (FIGS. 23 and 24). Further, component C was dissolved in the solvent $CD_3OD$ and analyzed by NMR (FIG. 25), and as a result it was estimated that component C is a novel substance containing a 5-memberred ring with conjugated bonds. The estimated structure thereof is shown in FIG. 26. Component D had UV absorption at a wavelength of about 230 nm (FIG. 27), and was detected at a RT of 30.28 minutes in HPLC (FIG. 28). However, when component D was analyzed again in HPLC by monitoring it at a terminal wavelength of 230 nm with a UV spectrum detector, it was confirmed that 2 components (D1, D2) having a difference (0.6 minute) in RT were present (FIG. 29). As a result of mass spectrometry of the two components, the component having UV absorption at 230 nm and a shorter RT had a molecular weight of 154 (D1). It was also estimated that the molecular weight of another component detected 0.6 minute later in RT was 220 (D2) (FIG. 30). It was confirmed that the revealed molecular weights of these components were 154 (D1), 168 (C), 192 (A), 206 (B) and 220 (D2) in the order of increasing molecular weight.

(5) Results of Bioassay
(a) Results of Bioassay of the Isolated and Purified Products from the Cultivation Using Medium A Results of Bioassay of the 4 Components Components A, B, C and D each at 5000 ppm were diluted and assayed at 5000 ppm, 2500 ppm, 1250 ppm and 625 ppm. As a result, it was confirmed that each of components A and E inhibited elongation of hyphae of Rhizoctonia solani at a concentration of 1250 ppm or more, while each of components B and D inhibited elongation of hyphae of Rhizoctonia solani at a concentration of 625 ppm or more.

(b) Results of Bioassay of the Isolated and Purified Products from the Culture Using Medium BI (I) Results of Evaluation Thereof Against the Bacteria Because of failure to form a circle of inhibited growth, it was considered that there is no or less activity in culture B (MW168) against the bacteria.

(II) The measurement result of antibacterial properties (MIC) against Staphylococcus is shown in Table 3.

As shown in Table 3, culture B (MW168) did not show antimicrobial properties at the concentrations used this time, and it was considered that there is no or less activity against Staphylococcus.

TABLE 3

| | | MIC (micro gram/ml) | | |
|---|---|---|---|---|
| No | Microorganisms | MW168 | DMPP | VCM |
| 1 | MRSA TH972 | >50 | >12.5 | 0.78 |
| 2 | MRSA TH973 | >50 | >12.5 | 0.78 |
| 3 | MRSA TH974 | >50 | >12.5 | 0.78 |
| 4 | MRSA TH975 | >50 | >12.5 | 0.78 |
| 5 | MRSA TH976 | >50 | >12.5 | 0.78 |
| 6 | MRSA TH1350 | >50 | 12.5 | 0.78 |
| 7 | MRSA TH1351 | >50 | 6.25 | 0.78 |
| 8 | MRSA TH1352 | >50 | >12.5 | 0.78 |
| 9 | MRSA TH1353 | >50 | >12.5 | 0.78 |
| 10 | MRSA TH1354 | >50 | >12.5 | 0.78 |
| 11 | MRSA TH948 | >50 | 1.56 | 0.78 |
| 12 | MRSA TH949 | >50 | 3.13 | 0.78 |
| 13 | MRSA TH950 | >50 | 3.13 | 0.78 |
| 14 | MRSA TH951 | >50 | 3.13 | 0.78 |
| 15 | MRSA TH952 | >50 | 1.56 | 0.78 |
| 16 | MRSA TH953 | >50 | 3.13 | 0.78 |
| 17 | MRSA TH954 | >50 | 3.13 | 0.78 |
| 18 | MRSA TH955 | >50 | 1.56 | 0.78 |
| 19 | MRSA TH956 | >50 | 3.13 | 0.78 |
| 20 | MRSA TH957 | >50 | 1.56 | 0.78 |
| 21 | S.aureu209P JC-1 | >50 | 1.56 | 0.78 |
| 22 | E.coliNIHJ JC-2 | >50 | 3.13 | >6.25 |

| Measurement concentration | |
|---|---|
| MW: 168 | 50~0.10 (micro gram/ml) |
| DMPP (methicillin) | 12.5~0.10 (micro gram/ml) |
| VCM (vacomycin) | 6.25~0.10 (micro gram/ml) |

Discussion

The 4 components of peptibols type containing Aib (α-aminoisobutyric acid) could be isolated from the culture in medium A. Some polypeptides of peptibols type produced by Trichoderma were already reported but did not agree with those isolated and purified this time. As a result of determination of the amino acid sequences of the 4 components, 3 components were estimated to be novel sequences (only component E could not be determined). Further, it was observed in the in vitro test that these components inhibit elongation of hyphae of Rhizoctonia solani (AG-1IA). From these results, it was revealed that the substances inhibiting elongation of hyphae of Rhizoctonia solani (AG-1IA) are produced in the rice cultivation extract of the present microorganism. It can not still be concluded that the substances of the present invention, upon contacting with hyphae, promote cytoplasmic aggregation as antagonistic action to kill the microorganism, but it is evident that the substances inhibiting hypha growth are produced in the rice extract of the present microorganism.

Figure 33:
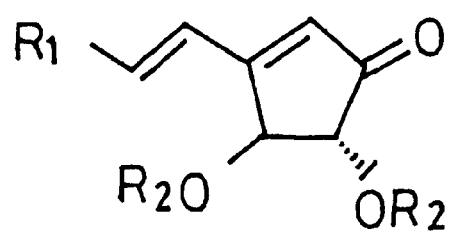
FIG. 33 is the chemical structure of novel substances (MW: 198) 1, 2 and 3.

The component isolated and purified from the culture in medium BI was a novel substance with a MW of 168 (3(3-hydroxy-cyclopropene 5-one-2-yl)2-propenoic acid), and by bioassay, this component was judged to have no or less activity. We estimate that the active substance is a compound having a MW in the vicinity of 168, and that said substance with a MW of 168 is a byproduct of the active substance. The molecular weights of the compounds having MWs in the vicinity of 168 are 154, 192, 206 and 220, and the difference among these molecular weights is 14. This different molecular weight corresponds to the molecular weight of one methyl group, and the difference in the number of methyl groups in the respective components may cause a difference in their activity. The present compound with a MW of 168 has a novel structure, but some compounds similar in structure were already reported. Among such compounds, a compound having the most similar structure to that of the present compound with a MW of 168 (FIG. 33) was found in Tottori University through screening of PGR activity, which is a novel substance represented by the formula of $C_8H_8O_5$ (MW: 198) reported to be an isolated and purified product metabolized by filamentous fungus Penicillium variable SOPP, but it is reported that the activity of this compound is low.

EXAMPLE 2

The plant activity promoter of this invention was applied to Ginga melon in farmland, and as a result, the following results were obtained. Place: Tagawa Farm, Yayoi, Kunshifu Town, Tokoro District, Hokkaido, JP. Period: From Apr. 23, 1999 to Jul. 29, 1999 Conditions: Agromic SK-10 (trade name of *Trichoderma harzianum* SK-5-5) was sprayed on melon bed soil at a density of 50 g/m².

$5 \times 10^7$ conidiospores/g had been allowed to adhere to MUGIMESHI stone having a diameter of 1 to 2 mm. Each of the test area and control area was 200 m², and the difference between the two areas lay in the presence or absence of Agromic SK-10. No agricultural chemical were used, and no additional fertilizer was used.

Agromic SK-10 was sprayed on Apr. 23, 1999, then seedlings were planted on Apr. 26, 1999, and fruits were harvested on and after Jul. 29, 1999. The average weight and sugar level of Ginga melon fruits are shown in Table 4.

TABLE 4

| Test Area | Sugar Level | |
|---|---|---|
| | Item | Sugar level |
| Treatment area | A | 17.0 (18.0) |
| | B | 16.8 (18.0) |
| Control area | C | 15.8 |
| | D | 15.6 |

The sugar level on 10 days after harvest is shown in the parentheses.

Characteristics in the Course of Inspection (1) The characteristics at the early stage were that the active attachment of roots was significant, leaves were large, stems were thick, and flowers were large.

(2) The characteristics at the middle stage in the treatment area were that vines (stems) were strong and rigid, which was significantly different from the control area, and there were no symptoms of seedling damping-off and vine-withering disease even though no agricultural chemical were used.

(3) The characteristics at the harvest stage were that the fruits were large and uniform, the net on the fruits was thick, and the tension of their flesh was outstanding.

(4) In inspection of their taste, the sugar level was constant throughout the flesh, the flesh was soft throughout near the pericarp, the sugar level was high, and the soft flesh tasted good (these characteristics were evidently different from those of melons in the control area).

(5) The fruits were dense and could be stored for a long period of time (as long as 1.5 times or more that of the fruits in the control area).

EXAMPLE 3

Place: Bioscience Laboratories, Meiji Seika Kaisha Ltd.

Period: From April to August, 1999

Conditions:

Seeded on April 6.

Germinated into seedlings on April 8 to 22.

The seedlings were planted on May 7, and Agromic SK-10 was sprayed at a density of $2 \times 10^7$/g in an amount of 30 to 40 g/m²

Cross-fertilized on June 4 to 7.

Harvested on July 12 to 23.

In the above period, an additional fertilizer was suitably applied and water was sprinkled. The results are shown in Table 5.

TABLE 5

| | Sugar Level | | | |
|---|---|---|---|---|
| | Item | | | |
| Division | Sugar level (Brix) | Sucrose | Glucose | Fructose |
| Treatment area | 16.9 | 13.10 | 1.36 | 0.47 |
| Control area | 15.4 | 10.76 | 1.85 | 1.31 |

Results

The sugar level was higher by 1.5% in the fruits in the treatment area. By applying SK-10, the sucrose level was increased, while glucose and fructose levels were suppressed. The increase in sugar level attained by applying SK-10 only once results from translocation of photosynthetic products and other activities brought about by interaction in the rhizosphere.

EXAMPLE 4

By applying the plant activity promoter of this invention onto sugar beet, the following results were obtained.

Place: Shikotan, Shari Town, Hokkaido, JP

Period: From Mar. 12, 1999 to Oct. 7, 1999

Conditions: A predetermined amount of Agromic SK-55 (trade name of *Trichoderma harzianum* SK-5-5 strain) was incorporated into about 30 kg soil in an upper part of a pot. The conidiospores were thus applied at a density of not less than $2 \times 10^8$/g. The soil was not sterilized. For fixing the microorganism, water was sprinkled once a week from the last ten days of March to the middle of April. On July 30, Agromic SK-55 previously diluted 100-fold was sprayed onto stems and leaves in an amount of 2 L/m². In both the treatment and control areas, fertilizers were applied in the same amount by the same manner, and the difference between the two areas is that sterilization was not conducted in the treatment area and treatment with Agromic SK-55 was not conducted in the control area.

Results: Thereafter, fruits were harvested on Jul. 29, 1998, and the real numbers in Table 6 and the ratios in Table 7 were obtained.

TABLE 6

Real Number

| | | | | Item | | | | | | |
|---|---|---|---|---|---|---|---|---|---|---|
| | Weight of stems and leaves | Weight of roots | Sugar content | Amount of sugar | | Brix | Net sugar ratio | Harmful non-sugar content | | |
| Area | (kg/10a) | (kg/10a) | (%) | (kg/10a) | T/R ratio | (%) | (%) | K | Na | A-N |
| Control area | 7,333 | 4,153 | 15.4 | 640 | 1.20 | 18.5 | 87.7 | 33.20 | 9.80 | 14.80 |
| Treatment area | 8,000 | 5,482 | 16.3 | 894 | 1.49 | 19.4 | 88.6 | 33.90 | 9.20 | 15.90 |

TABLE 7

Ratio

| | | | | Item | | | | | | |
|---|---|---|---|---|---|---|---|---|---|---|
| | Weight of stems and leaves | Weight of roots | Sugar content | Amount of sugar | | Brix | Net sugar ratio | Harmful non-sugar content | | |
| Area | (kg/10a) | (kg/10a) | (%) | (kg/10a) | T/R ratio | (%) | (%) | K | Na | A-N |
| Control area | 100 | 100 | 100 | 100 | 100 | 100 | 100 | 100 | 100 | 100 |
| Treatment area | 109 | 132 | 106 | 140 | 124 | 105 | 101 | 102 | 94 | 107 |

According to the above example, the weight of roots was increased by 32%, and the amount of sugar was increased by 40%. Accordingly, the yield in the same area was increased by 40%, indicating an outstanding result.

The significant increase in the yield achieved by incorporation of Agromic SK-55 at the germinating stage and by spraying Agromic SK-55 on July 30, as shown in the above example, suggests that roots and stems of sugar beet are activated with Agromic SK-55, whereby absorption of nutrients is rationalized and enhanced, and cellular differentiation is also normalized.

For sugar beet, further advantages will be brought about by studying the amount of Agromic SK-55 applied and the timing of application in treatment of seeds, incorporation into soil, and intermediate spraying.

EXAMPLE 5

By applying the plant activity promoter of this invention onto paddy rice plants, the following results were obtained.

Places:
  Sasaki Farm, Kiyota, Sapporo City, Hokkaido, Japan.
  Hiyama Farm, Tajin Town, Yubari District, Hokkaido.
  Takahashi Farm, Hokuryu Town, Uryu District, Hokkaido.
Period:
  May 6 to Sep. 16, 1999
Conditions: Varieties: Hoshinoyume, Kirara 397
  Amount of Agromic SK-10 sprayed (trade name of *Trichoderma harzianum* SK-5-5)
  A . . . 50 g/m$^2$, 2×10$^8$ conidiospores/g
  B . . . 100 g/m$^2$, 2×10$^8$ conidiospores/g By cultivating rice plants under the conditions described above, the results in Table 8 (Sasaki Farm), Table 9 (Hiyama Farm) and Table 10 (Takahashi Farm) were obtained.

TABLE 8

Sasaki Farm

| | | | Item | | | |
|---|---|---|---|---|---|---|
| Area | Number of grains | Number of ears | Plant density | Rate of maturity | Weight of thousand grains | Yield Kg/1000 m$^2$ |
| 50 g area | 34 | 33 | 23.333 | 67% | 20.2 | 354 Kg (36% increase) |
| 100 g area | 32 | 33 | 23.333 | 70% | 20.3 | 350 Kg (34% increase) |
| Control area | 34 | 27 | 23.333 | 63% | 19.3 | 260 Kg |

Variety, Hoshinoyume; mat, 3.3 m$^2$/77 plants; harvest day, Sep. 2, 1999.

TABLE 9

Hiyama Farm

| Area | Number of grains | Number of ears | Planting density | Rate of maturity | Weight of thousand grains | Yield | Protein content |
|---|---|---|---|---|---|---|---|
| 50 garea | 51 | 31 | 24.242 | 75% | 22.3 | 917 Kg (124% increase) | 7.2 |
| 100 garea | 43 | 37 | 24.242 | 75% | 22.6 | 350 Kg (78% increase) | — |
| Control area | 55 | 22 | 24.242 | 75% | 20.0 | 205 Kg | 7.8 |

Variety, Kirara 397; pot, 3.3 m²/80 plants; harvest day, Sept. 3, 1999.

It is estimated that as the protein content is decreased, rice tastes better.

TABLE 10

Takahashi Farm

| Area | Number of grains | Number of ears | Plant density | Rate of maturity | Weight of thousand grains | Yield Kg/1000 m² |
|---|---|---|---|---|---|---|
| 50 g area | 70 | 28 | 24.242 | 75% | 24.0 | 855 Kg |

Variety, Kirara 397; mat, 3.3 m²/80 plants; harvest day, Sep. 16, 1999.

It was confirmed in the above example that the protein content and amylose content in Kirara 397 in the treatment areas were lower by 4 to 6 points and 1 to 3 points respectively than in the control area (1 point=0.5).

The degree of taste was determined to be 91.0 on average. On the other hand, the degree of taste of commercial rice regarded as tasting good was 88.0 at the maximum, so it can be said that the rice obtained this time showed the highest degree of taste.

From the above result, it was confirmed that the low-chemical organic farming according to the present invention can not only control disease-causing bacteria and harmful insects by activating rice plants, but also improve tastes and increase the yield (higher by 20 to 50%) by deriving original forces from the plants.

EXAMPLE 6

By applying the plant activator of this invention onto corn plants, the following results were obtained.

Place: Bioscience Laboratories, Meiji Seika Kaisha Ltd.

Period: From April, 1999 to Aug. 30, 1999

Used microorganism: Agromic SK-10 ($2 \times 10^7$/g)

Application method: In the second week of germination, the microorganism was applied to soil and water was sprayed (150 ml/pot).

Application: Under the above conditions, the microorganism was applied according to Table 11.

TABLE 11

| Area | Test Area | Standard Amount for Application | Amount for Application |
|---|---|---|---|
| No. 11 | 1 | Not applied | 0 |
| No. 12 | 2 | 20 g/m² | 1 g/pot, 1/2000 a |
| No. 13 | 3 | 40 g/m² | 2 g/pot, 1/2000 a |
| No. 14 | 4 | 200 g/m² | 10 g/pot, 1/2000 a |

Environment: Natural light (outdoor); daytime, 25 to 38° C.; nighttime, 25 to 28° C.; ground temperature, 25 to 34° C.

By cultivating and harvesting corns as described above, the results in Table 12 were obtained.

TABLE 12

| Test area No. | Number of days for maturity | Weight of bare corns | Average sugar level (Brix) | Significant difference |
|---|---|---|---|---|
| 1 | 15 | 137.3 g | 18.9 | |
| 2 | 16 | 151.6 g | 20.0 | 5% |
| 3 | 16 | 142.9 g | 19.8 | 5% |
| 4 | 17 | 146.2 g | 20.4 | 1% |

As described above, the effect of enlarging corns and the improvement in sugar level were recognized. There was no significant difference among the treatment areas to which different amounts of Agromic SK-10 were applied. That is, there was no significant difference between the 20 g/m² and 200 g/m² treatment areas, and it is estimated that once the plants are activated by applying Agromic SK-10 only once after germination, the effect thereof on corn is continued until harvest.

Accordingly, if the amount of new amino acids formed by Agromic SK-10 is sufficient for activation, the effect is sufficiently demonstrated even if the amount of Agromic SK-10 is not higher than 20 g/m².

For this reason, it is considered that the effect is sufficiently demonstrated by Agromic SK-10 even in an amount of not higher than 20 g/m² in soil under conditions necessary for growth of Agromic SK-10. The amount of Agromic SK-10 applied may be determined by the minimum density of Agromic SK-10 at which it can grow. It therefore follows that under conditions necessary for growth Agromic SK-10, corn plants may be grown for a predetermined period of time after germination.

EXAMPLE 7

Agromic SK-10 (trade name of *Trichoderma harzianum* SK-5-5) was applied into a bed soil for onion seedlings, and the seedlings and the effect of Agromic SK-10 on growth promotion after planting were examined as follows:

(1) Test Materials:
(a) Test Seeds: Seeds not Treated with the Chemical, Super High Gold.
(b) Test Microorganism: Agromic SK-10 ($5 \times 10^8$ CFU of Living Microorganism *Trichoderma harzianum* SK-5-5 from Hokkaido Green Kosan, Incorporated)
(c) Test Place: Konma, Shimo District, Kisaradzu City, Chiba Pref., JP (2) Test Method:
(a) Preparation of a bed for seedlings: The bed for seedlings was composed of sandy soil from Shimonoyama in Chiba Pref., and a field where sweet corn had previously been cultivated was used. The soil in this field was weakly acidic at about pH 6.0 so that 15 days before application of Agromic SK-10, 50 g slaked lime for regulating the pH, 1 kg of completely matured compost (rice husk-containing compost based on cow dung) and 20 g CDU were applied every 1 $m^2$ field, followed by cultivation.

(b) Method of Applying Agromic SK-10:

Application day: Sep. 11, 1999

Four days before seeding, 50 g granules of test microorganism Agromic SK-10 were applied every 1 $m^2$ of the prepared bed for seedlings and kneaded therein to a depth of 3 to 5 cm from the ground, and tap water was sprinkled to such an extent that the soil was not made too moist (i.e. to such an extent that a mass of soil could be formed by hand, that is, the optimum moisture condition for growth of filamentous fungi).

(c) Seeding and Management After Application of Agromic SK-10

Seeding day: Sep. 15, 1999

Because of the severe lingering summer heat (high temperature and dryness) during the test period, it was necessary to keep the ground temperature at about 20 to 25° C. in order to permit the Trichoderma microorganism to be multiplied and fixed on the soil for seedlings and to facilitate germination of onion seeds. Rye straw was laid to a thickness of 2 to 3 cm from the ground on both the areas, and Kanreisha (cloth for preventing heating) was placed thereon.

About 70 onion seeds/50 cm were seeded by drilling, then covered with soil, sprayed with water and covered in the manner described above until germination was initiated.

After germination, the laid straw was removed, and the seedlings were covered with a tunnel of Kanreisha for about 1 month. For planting the seedlings in the field, the tunnel was removed, and 20 g CDU chemical fertilizer mixed with compost was applied between lines every 1 $m^2$ cultivated field. The seedlings were grown for producing young plants with stems of 0.5 to 0.6 cm in diameter and leaves. of 5 to 6 cm in length.

(d) Planting the Seedlings in the Field:

Day when the seedlings were planted in the field: Nov. 7, 1999 (53 days after seeding)

The soil in this field was alluvial soil, that is, weakly acidic soil at about pH 6.0, in which sweet potato had previously been cultivated. 60 kg slaked lime, 500 kg completely matured compost, 60 kg bone powder and 60 kg rice cake were applied every 10 ares, followed by cultivation. After 1 week, a ridge of 1 m in width and 3 lines for planting were prepared on the field, and 20 kg CDU and 10 kg calcium superphosphate were incorporated into 300 kg completely matured compost and then applied to a long narrow channel on the field. The seedlings were planted in the order of a decreasing size in the channel at 15-cm intervals.

(3) Study Results:
(a) State of germination and growth: There was little difference in germination between the non-treatment area and the treatment area, but after 1 week, slight damping-off occurred in the seedlings in the non-treatment area. In growth of the seedlings thereafter, there was no difference on and before 25 days, but after the tunnel was removed and additional fertilities were added (that is, on and after 35 days after seeding), there occurred differences between the two areas; that is, in the treatment area, the color of leaves became darker, and vigorous growth was observed.

(b) Inspection of Seedling Growth:

(A) Growth conditions of the seedlings before planting in the field: Date of inspection, Nov. 7, 1999 (53 days after seeding). Detailed data are shown in Table 13.

Good seedlings (in terms of the number of seedlings of large and middle size) were 78% in the treatment area and 65% in the non-treatment area. By application of Agromic SK-10, the ratio of good seedlings was increased by 13%. There was no seedling with a diameter of 0.7 mm or more. Concerning the promotion effect in the section treated with Agromic SK-10, the index of growth was increased, the growth was vigorous and the amount of roots was increased, as shown in Table 13. By comparing the degrees of growth promotion, it was recognized that the degree of growth was higher by 27% in the SK-10-treated area than in the non-treatment area.

(B) Inspection of growth after planting the seedlings in the field: Conditions of growth before winter were examined.

Figure 34:
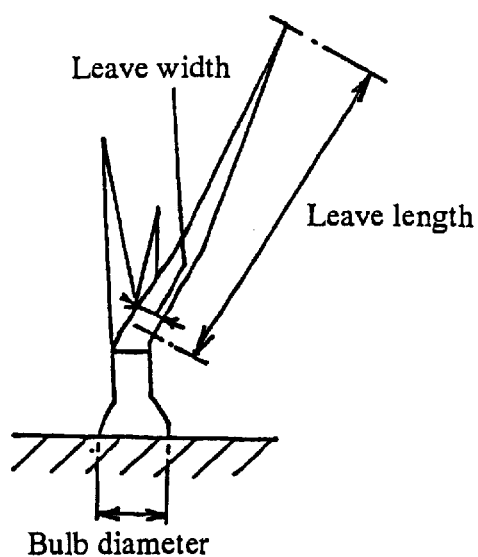
FIG. 34 shows examination of growth of onion before winter.

Method of inspection: Inspected by the method in FIG. 34.

Results: The results are shown in Table 14.

Figure 35:
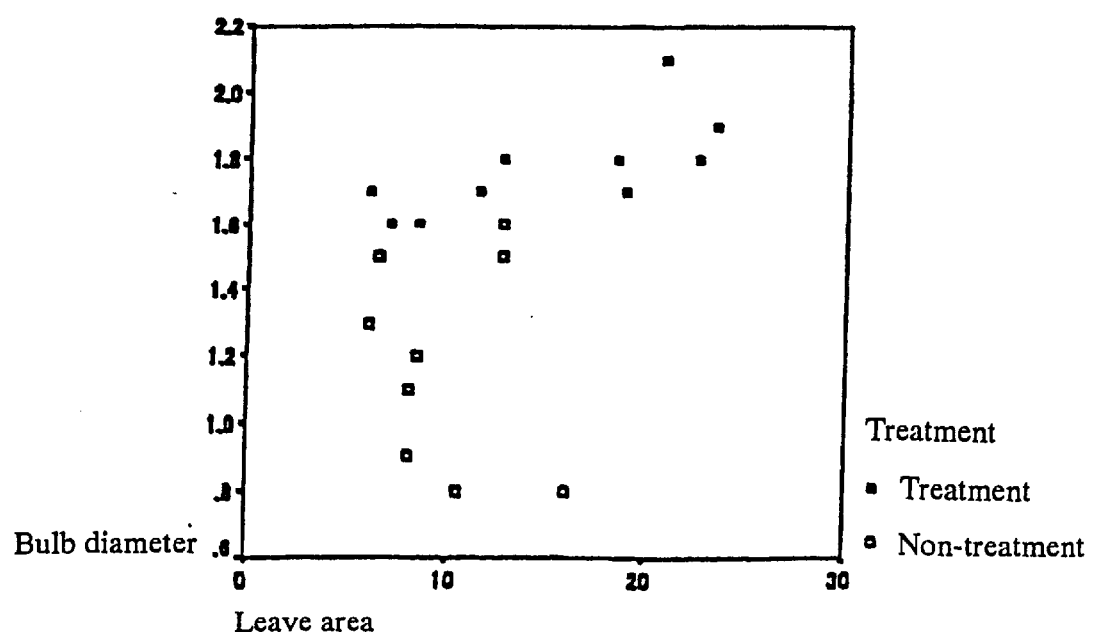
FIG. 35 shows a correlation between the diameter of onion bulb and the area of leaves.

The area treated with Agromic SK-10 showed an increased number of leaves (higher by 0.4 leave), the degree of growth promotion of 152.5% and 154.7% bulb diameter, as compared with those of the non-treatment area. The effect of growth promotion was clearly recognized even by observation with the naked eye. The area treated with Agromic SK-10 showed a larger amount of roots, better rooting, better adhesion of soil to roots and a larger number of hair roots than those in the non-treatment area. In the area treated with Agromic SK-10, the area of leaves was correlated with the diameter of bulb (FIG. 35, Tables 15 and 16).

TABLE 13

Growth of seedlings before planting in the field (Number of seedlings in a 50-cm interval on Day 53 after seeding)

| | Size of seedlings | | | | | | |
|---|---|---|---|---|---|---|---|
| Area/index | Large 5 | Middle 3 | Small 1 | Number of total seedlings Totaled index | Average index of growth[a] | Average promotion[b] (%) | Remarks |
| Number of seedlings in | 13 | 13 | 14 | 40 | 2.91 | 100 | Large: Seedling with |

TABLE 13-continued

Growth of seedlings before planting in the field (Number of seedlings in a 50-cm interval on Day 53 after seeding)

| Area/index | Size of seedlings | | | Number of total seedlings Totaled index | Average index of growth[a] | Average promotion[b] (%) | Remarks |
|---|---|---|---|---|---|---|---|
| | Large 5 | Middle 3 | Small 1 | | | | |
| non-treatment area | | | | | | | 0.6 to 0.5 cm diameter, index 5 |
| Number of seedlings × index | 65 | 39 | 14 | 118 | | | Middle: Seedling with 0.5 to 0.4 cm diameter, index 3 |
| Number of seedlings in treatment area | 23 | 9 | 9 | 41 | 3.68 | 126.5 | |
| Number of seedlings × index | 115 | 27 | 9 | 151 | | | Small: Seedling with 0.3 cm or less diameter, index 1 |

[a]Average index of growth refers to number of seedlings × totaled index/number of total seedlings
[b]Average promotion refers to average index of growth/average index of growth in non-treatment area × 100

TABLE 14

Inspection of growth before winter (date of inspection: Dec. 23, 1999)

| Area | Item | | | |
|---|---|---|---|---|
| | Non-treatment area | Treatment area | Growth promotion (%) | Remark |
| Average number of leaves | 3.7 | 4.1 | 110.0 | Leave area = length of maximum leave × width of maximum leave |
| Average area (cm²) | 9.66 | 14.94 | 152.5 | |
| Average bulb diameter (cm) | 1.16 | 1.77 | 154.7 | |

TABLE 15

Coefficient of correlation between bulb diameter and leave area in the treatment area

| Area | Evaluation item | Item | |
|---|---|---|---|
| | | Bulb diameter | Leave area |
| Bulb diameter | Pearson's coefficient of correlation | 1.000 | 0.713 |
| | Probability of significance (both sides) | | 0.021 |
| | N | 10 | 10 |
| Leave area | Pearson's coefficient of correlation | 0.713 | 1.000 |
| | Probability of significance (both sides) | 0.021 | |
| | N | 10 | 10 |

The coefficient of correlation is significant at 5% standard (both sides).

TABLE 16

Coefficient of correlation between bulb diameter and leave area in the non-treatment area

| Area | Evaluation item | Item | |
|---|---|---|---|
| | | Bulb diameter | Leave area |
| Bulb diameter | Pearson's coefficient of correlation | 1.000 | −0.117 |
| | Probability of significance (both sides) | | .748 |
| | N | 10 | 10 |
| Leave area | Pearson's coefficient of correlation | −0.117 | 1.000 |
| | Probability of significance (both sides) | 0.748 | |
| | N | 10 | 10 |

EXAMPLE 8

Agromic SK-10 was applied to a bed soil for cabbage seedlings, and the seedlings and the effect of promoting growth thereof after planting in a field were examined as follows:

(1) Used Materials:
(a) Test Seeds: Seeds not Treated With Chemicals.
(b) Test Microorganism: Agromic SK-10 (5×10⁸ CFU of *Trichoderma harzianum* SK-5-5 from Hokkaido Green Kosan, Incorporated)
(2) Place: Yoshida Farm, Narita City, Chiba Pref., JP
(3) Outline:
(a) Date of Application: Sep. 15, 1999
(b) Date of Seeding: Sep. 19, 1999
(c) Soil bed: 50 g slaked lime was sprayed every 1 m² field in order to neutralize sandy soil of a pH value of about 6.0. Two weeks before application of Agromic SK-10, 1 kg completely matured compost was applied every 1 m² field, followed by cultivation.

Before seeding, 50 g Agromic SK-10 was applied every 1 m² field. Then, the soil was kneaded to a depth of about 5 cm from the ground, and about 3 liter/m² water was sprinkled to such an extent that the soil was not made too moist (that is, to such an extent that a mass of soil could be formed by hand).

(2) Date of Inspection: Dec. 23, 1999 (94 days After Seeding)

On the date of inspection, it was recognized that the leaves in the treatment area were darker, thick and firm, and the plant rapidly headed up.

What is claimed is:
1. A composition for imparting antimicrobial properties against filamentous fungi to plants, which comprises the following components A, B, C and D:

Component A: Ac-Aib-Ala-Aib-Aib-Aib-Aib-Gln-Aib-Aib- . . . with a molecular weight of 192;

Component B: Ac-Aib-Ala-Aib-Aib-Val-Aib-Gln-Aib-Aib- . . . with a molecular weight of 206;

Component C:

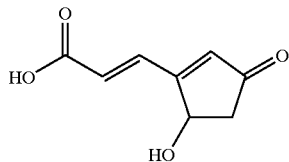

with a molecular weight of 168; and

Component D: Ac-Aib-Ala-Aib-Aib-Aib- . . . with a molecular weight of 154 or 220.

2. A composition for imparting antimicrobial properties against a kind of microorganism (*Staphylococcus aureus* 209p) to plants, which comprises the following components A, B, C and D:

Component A: Ac-Aib-Ala-Aib-Aib-Aib-Aib-Gln-Aib-Aib- . . . with a molecular weight of 192;

Component B: Ac-Aib-Ala-Aib-Aib-Val-Aib-Gln-Aib-Aib- . . . with a molecular weight of 206;

Component C:

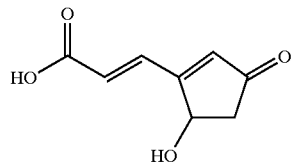

with a molecular weight of 168; and

Component D: Ac-Aib-Ala-Aib-Aib-Aib- . . . with a molecular weight of 154 or 220.

* * * * *